(12) United States Patent
Broyer et al.

(10) Patent No.: US 10,365,191 B2
(45) Date of Patent: Jul. 30, 2019

(54) METHOD FOR TREATING BIOLOGICAL SAMPLES, ESPECIALLY FOOD SAMPLES

(71) Applicant: BIOMERIEUX, Marcy l'Etoile (FR)

(72) Inventors: Patrick Broyer, Saint Cassien (FR); Pradip Patel, Grezieu la Varenne (FR); Nicole Pamme, Beverly (GB); Jean-Claude Raymond, Bessenay (FR)

(73) Assignee: BIOMERIEUX, Marcy l'etoile (FR)

( * ) Notice: Subject to any disclaimer, the term of this patent is extended or adjusted under 35 U.S.C. 154(b) by 0 days.

(21) Appl. No.: 15/521,567

(22) PCT Filed: Oct. 23, 2015

(86) PCT No.: PCT/FR2015/052848
§ 371 (c)(1),
(2) Date: Apr. 24, 2017

(87) PCT Pub. No.: WO2016/062974
PCT Pub. Date: Apr. 28, 2016

(65) Prior Publication Data
US 2017/0315033 A1  Nov. 2, 2017

(30) Foreign Application Priority Data

Oct. 24, 2014 (FR) .................................... 14 60258

(51) Int. Cl.
*C12Q 1/04* (2006.01)
*G01N 1/40* (2006.01)
*C12N 13/00* (2006.01)
*G01N 15/14* (2006.01)
*G01N 33/12* (2006.01)
*G01N 15/10* (2006.01)
*G01N 15/00* (2006.01)

(52) U.S. Cl.
CPC ............ *G01N 1/4077* (2013.01); *C12N 13/00* (2013.01); *G01N 15/1459* (2013.01); *G01N 15/1484* (2013.01); *G01N 33/12* (2013.01); *G01N 2001/4088* (2013.01); *G01N 2001/4094* (2013.01); *G01N 2015/0088* (2013.01); *G01N 2015/1006* (2013.01); *G01N 2015/1081* (2013.01); *G01N 2015/142* (2013.01); *G01N 2015/1409* (2013.01); *G01N 2015/149* (2013.01)

(58) Field of Classification Search
CPC .................................. C12Q 1/04; C12Q 1/10
See application file for complete search history.

(56) References Cited

U.S. PATENT DOCUMENTS

2015/0079597 A1   3/2015  Flandrois et al.

FOREIGN PATENT DOCUMENTS

| FR | 2 985 520 A1 | 7/2013 |
| WO | 2014/046605 A1 | 3/2014 |

OTHER PUBLICATIONS

Augustsson et al., "Decomplexing biofluids using microchip based acoustophoresis," Lab on a Chip, 2009, vol. 9, pp. 810-818.
(Continued)

*Primary Examiner* — Rosanne Kosson
(74) *Attorney, Agent, or Firm* — Oliff PLC

(57) ABSTRACT

A method for treating a biological sample, preferably a food sample which may contain one or more species of interest, including a step of decomplexification by acoustophoresis.

14 Claims, 15 Drawing Sheets

(56) References Cited

OTHER PUBLICATIONS

Lenshof et al., "Acoustofluidics 8: Applications of acoustophoresis in continuous flow microsystems," Lab on a Chip, 2012, vol. 12, pp. 1210-1223.
Ståhlberg et al., "The workflow of single-cell expression profiling using quantitative real-time PCR," Expert Review of Molecular Diagnostics, 2014, vol. 14, No. 3, pp. 323-331.
Lenshof et al., "Emerging Clinical Applications of Microchip-Based Acoustophoresis," Journal of Laboratory Automation, 2011, vol. 16, No. 6, pp. 443-449.
Autebert et al., "Microfluidic: An innovative tool for efficient cell sorting," Methods, 2012, vol. 57, pp. 297-307.
Tarn et al., "On-chip processing of particles and cells via multilaminar flow streams," Analytical and Bioanalytical Chemistry, 2014, vol. 406, pp. 139-161.
Jan. 11, 2016 International Search Report issued in International Patent Application No. PCT/FR2015/052848.
Jan. 11, 2016 Written Opinion of the International Searching Authority issued in International Patent Application No. PCT/FR2015/052848.

Section A-A

Section B-B

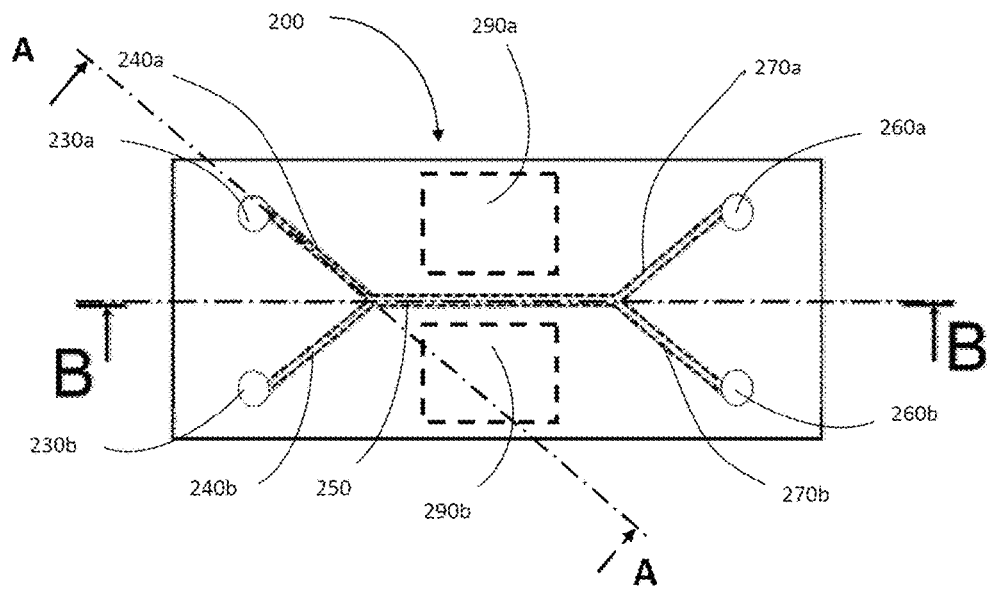
Figure 4
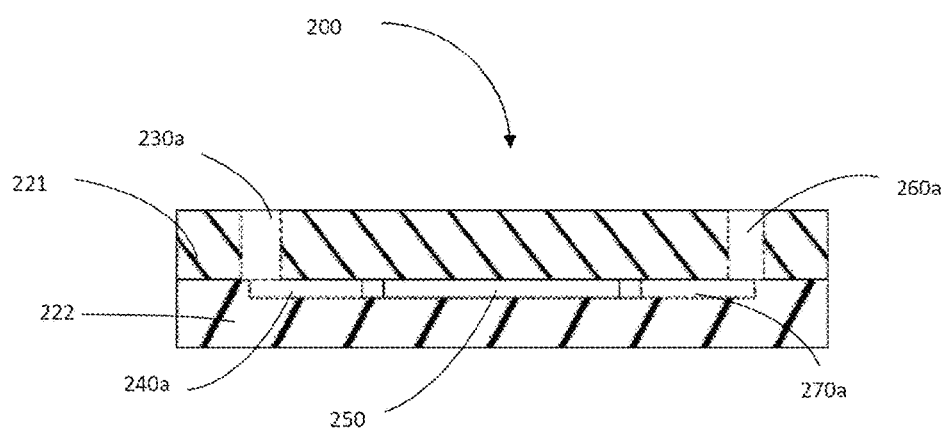
Figure 5a – Section B-B

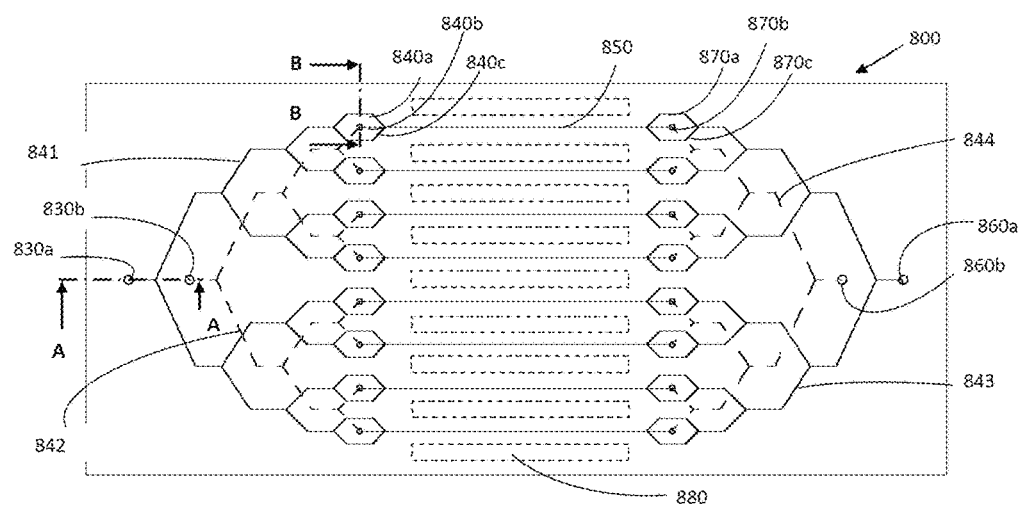
Figure 11
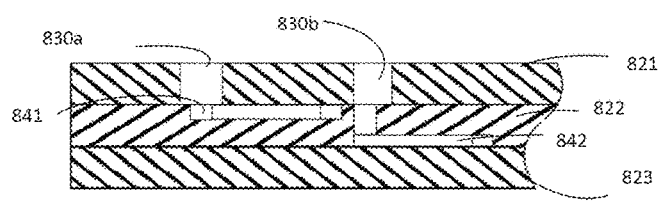
Figure 12a – Section A-A
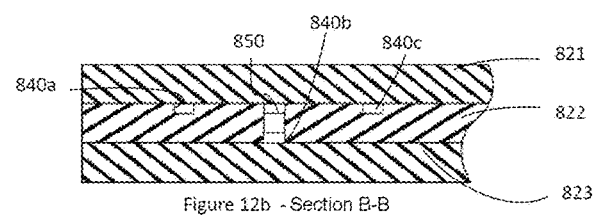
Figure 12b – Section B-B

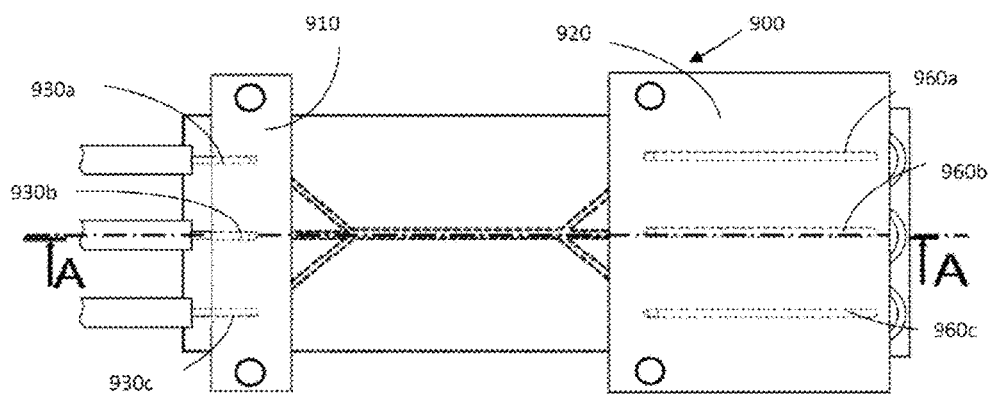
Figure 13a
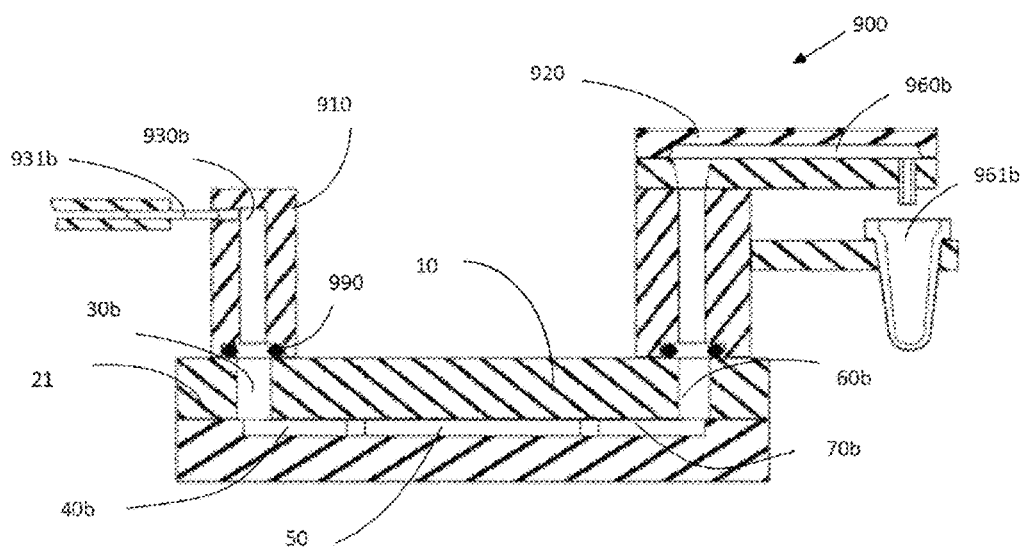
Figure 13b - Section A-A

METHOD FOR TREATING BIOLOGICAL SAMPLES, ESPECIALLY FOOD SAMPLES

BACKGROUND

Field of Disclosed Subject Matter

The method and the devices according to the invention are of interest in the treatment of biological samples, in particular in the field of tests on food samples.

Description of Related Art

Food poisoning has for a long time constituted a threat to public health. A total of 19 531 infections, 4563 hospitalizations and 68 deaths associated with food poisoning, for example caused by *Salmonella, Escherichia coli* O157:H7, *Listeria* or *Campylobacter*, have been reported in 2012 by the Food Net network.

Conventional methods for searching for the presence of pathogenic agents in foods comprise:
- pre-enrichment of the sample in order to enable the return to growth phase of the pathogenic agent suspected of being contained and also of the intrinsic flora naturally present in the sample;
- selected enrichment by culturing in order to inhibit the growth of the intrinsic flora, making it possible to obtain a better concentration ratio between the pathogenic agent and the "background noise";
- selective culture on a Petri dish so as to allow the growth of the specific pathogenic agent, while at the same time limiting or inhibiting the growth of the intrinsic flora.

By virtue of this method, the pathogenic agent, if it is present, is detected as a "typical" colored colony on the Petri dish.

Furthermore, various biochemical or immunological techniques, or serological or else genetic tests can allow finer identification of the pathogenic agent.

This conventional method is thus quite laborious in terms of handling, and requires much more time and labor. By way of example, the detection and identification of *Salmonella* using this method can take from 3 to 5 days.

Many rapid detection systems, including based on immunology (for example the VIDAS® 3 device of the applicant) or molecular biology techniques are also available and make it possible to reduce the analysis time by 24 h to 48 h, depending on the types of pathogenic agents and on the matrix of the food sample.

Because of the worldwide food supply chain and the regulatory pressures aimed at increasing food safety for consumers, there is an increased need to provide a faster method which makes it possible to detect and/or identify pathogenic agents in food matrices. Furthermore, the regulatory authorities for food safety impose the confirmation of an analytical result by a method different than that having provided the first result.

For this purpose, several approaches based on the capture and the concentration of the target pathogenic agent from complex samples before detection have thus been reported. These methods use in particular bacteriophage proteins or immunomagnetic particles covered with magnetic micro- or nanobeads. These techniques allow faster and more robust detection of the pathogenic agent from certain food matrices owing to the reduction in background interferences (for example inhibitors of PCR for molecular detection), and also the concentration of the pathogenic agent. However, these techniques are particularly limited for analysis on food matrices comprising fatty components, since said components can hinder the recovery of the capture beads. Furthermore, these techniques are relatively expensive, which is totally incompatible with routine use.

BRIEF SUMMARY

With regard to the problems presented above, an objective of the present invention aims to develop a device and the process(es) associated therewith making it possible:
- to provide a simplified and universal process which makes it possible to treat and analyze food samples of various types, including those comprising a large number of fatty or particulate components;
- to provide a process guaranteeing the viability of the particles, cells or molecules of interest, which can additionally be analyzed, in particular the viability of the pathogenic agents such as bacteria;
- to provide a process which allows a faster return to growth phase of the pathogenic agents and the intrinsic flora present in the biological sample;
- to separate and/or to concentrate particles, cells or molecules of interest at high flow rates, in particular flow rates greater than 1 µl/min per separation channel for treating significant volumes of samples (several ml if necessary);
- to limit the production of non-specific elements which may distort the final result of the analysis;
- to limit as much as possible the risks of contamination of the sample and/or of the environment and/or of the laboratory technician;
- to simplify the food sample preparation protocol, in order to reduce the operating time, the number of materials and consumables used and the risk of errors and to improve reproducibility;
- to provide devices and a method compatible with all of the known methods of analysis (microbiology, culture, virology, bacteriology, immunoassays, metasequencing, PCR, etc.);
- to decomplexify a food sample, optionally capture, and analyze the particles of interest that may be present in the sample in continuous flow,
- to decomplexify the food sample by separating the non-specific particles toward one of the outlets of a microfluidic device.
- to provide several associated microfluidic devices, supports and systems capable of carrying out methods for treating biological samples by acoustophoresis, in particular methods according to the invention.

The present invention relates to a method allowing the decomplexification of biological samples, in particular food samples, thus allowing the capture and/or analysis of microorganisms which are contained or which may be contained in the biological sample.

In order to achieve this objective and to overcome the drawbacks of the abovementioned methods, the invention relates to a method for treating a biological sample which may contain one or more species of interest, comprising a decomplexification step, this decomplexification step comprising the following steps
- introducing all or part of this sample into a first inlet orifice of an acoustophoresis device,
- introducing a buffer solution into a second inlet orifice of the acoustophoresis device,
- said inlet orifices being fluidically connected to at least two outlet orifices by a separation channel, the buffer and the sample being introduced at respective flow rates capable of generating a laminar flow in the separation channel, carrying out a step of separation of said biological sample by acoustophoresis so as to promote the concentration of the non-specific particles, such as food debris, present in the sample, in at least one of the outlet orifices of said acoustophoresis device.

The term "non-specific particles" is intended to mean particles which can impair or limit the capture and/or the detection of microorganisms in the biological sample. Such particles may be, by way of example, food debris, compounds of muscle fibers, fatty lumps, pulp, micelles, coagulum, etc.

Following this method, at least one of the outlet orifices of the device exhibits a decomplexified sample, that is to say its concentration of non-specific particles, such as food debris, is reduced. This decomplexification step is thus analogous to a purification step in so far as it facilitates the detection and the subsequent analysis of the microorganisms present in the sample.

Indeed, the majority of the non-specific particles are separated by the acoustophoresis separation step, since said particles have a higher volume and/or density and/or a lower compressibility than the microorganisms, they are therefore more subject to the acoustic radiation pressure and are concentrated in one of the outlet orifices. Conversely, the intrinsic flora and potentially the species of interest is (are) less subject to the effect of the acoustic wave by virtue of its (their) size, its (their) density and its (their) compressibility. Said species will thus be distributed predominantly by the circulation of the fluid containing them at the time they are introduced into the device. Depending on the geometry of the device and the orientation of the acoustic wave in the separation channel, the non-specific particles can in particular be separated in the direction of an outlet orifice of which the conveying channel has an axis similar to and in the extension of that of the separation channel. This separation in continuous flow toward a "central" outlet orifice, the channel of which has an axis similar to that of the separation channel, can be carried out by applying an acoustic wave having a pressure node substantially centered about the longitudinal axis of the separation channel. The distribution of the intrinsic flora and potentially the one or more species of interest can, depending on its (their) volume, its (their) density and its (their) compressibility, be equitable between the outlet orifices or concentrated in at least one outlet orifice, other than that where the non-specific particles are concentrated.

Following this method, at least one of the outlet orifices of the device, other than that comprising the enriched and decomplexified sample, exhibits a concentrated sample, that is to say its concentration of non-specific particles is increased.

Buffer solutions which can be used are, for example, and in a non-limiting manner:

Neutral buffers, for example water, a 0.85% NaCl solution, phosphate buffered saline (PBS), etc.

Non-specific (generic) buffers for return of microorganisms to growth. By way of example, these buffers may be of BHI (brain heart infusion broth), TSB (trypticase soy broth) or BPW (buffered peptone water) type.

Microorganism-specific buffers for return to growth. By way of example, these buffers may be of the type: Fraser 1/2, LX broth (*Listeria* Xpress broth; Ref. 42626 bioMérieux, France), LMX broth (*Listeria Monocytogenes* Xpress broth; bioMérieux, France) or SX broth (*Salmonella* Xpress broth; Ref. 42118 bioMérieux, France).

Buffers with a density that is either lower or higher than the density of the biological sample; the density of the sample is supposed to be close to 1. By way of example, these buffers can comprise: (silanized) colloidal silica, Iohexol (Nycodenz®), Iodixanol (OptiPrep™), Ficoll 400, Dextran 70, Dextran 200, Dextran 500, sucrose, cesium chloride, perfluorocarbon fluids, mineral oils, silicone oils, oils for immersion microscope lenses, Pluronic® F127, polyethylene oxide, polyvinyl alcohol, hydroxypropylmethylcellulose, xanthan gum.

Advantageously and in so far as the device used with the method according to the invention comprises at least three inlet orifices and three conveying channels of these orifices to the separation channel, two different buffer solutions are introduced into two different inlet orifices. The use of two different buffer solutions makes it possible to facilitate the passage of certain particles or microorganisms from one liquid introduced to another during the separation step, by adjusting in particular the differences in density between the buffer solutions introduced.

Optionally, the treatment method according to the invention can comprise a prior step of filtration of the biological sample through a membrane before the introduction of said biological sample into the acoustophoresis device. This step can in particular be carried out by introducing the sample into a bag comprising a compartment delimited by a filtering membrane, the sample being taken behind the membrane before being introduced so as to remove the coarsest debris, preferentially the debris greater than approximately 90 μm in size.

More particularly, the biological sample is introduced into an acoustophoresis device so as to be conveyed by at least two conveying channels to the separation channel, the device being arranged to obtain a laminar flow in the separation channel between the flows of sample and of buffer solution originating from the conveying channels.

The treatment method according to the invention makes it possible, using a non-enriched food sample, to carry out for example a step of counting the total flora of the sample.

In this respect, the invention also relates to a treatment method as described above and comprising a step of counting the total flora present in the biological sample following the separation step. This step can in particular be carried out by inoculating a volume of the decomplexified sample onto a non-specific culture medium, for example a Trypticase Soy Agar medium (TSA; bioMérieux, France).

Advantageously, the treatment method as described above can comprise carrying out a step of enrichment of the biological sample, preferentially by incubation in the presence of a culture medium, before the introduction of said biological sample into the acoustophoresis device. This incubation step makes it possible in particular to increase the concentration of the species of interest that may be contained and optionally detected in the biological sample. The culture medium that can be used may be specific or non-specific. By way of example of culture medium, mention may be made of Buffer Peptone Water broth (BPW; bioMérieux, France), as non-specific growth medium, or else the LX (*Listeria* Xpress broth; Ref. 42626 bioMérieux, France), LMX (*Listeria Monocytogenes* Xpress broth; bioMérieux, France) or SX (*Salmonella* Xpress broth; Ref. 42118 bioMérieux, France) broths respectively studied for the specific growth of *Listeria* spp./*Listeria monocytogenes* and *Salmonella*. By way of example of non-specific culture medium, mention may be made of Trypticase Soy broth (TSB; bioMérieux, France).

Advantageously, the treatment method as described above can comprise, following the step of separation by acoustophoresis, carrying out a step of specific or non-specific capture of the one or more species of interest on a capture support, followed by a step of concentration by immunological separation or affinity separation. This capture step can be carried out on line, also called "continuous flow", directly following the separation step. For this purpose, the decomplexified biological sample is brought into contact with optionally magnetic capture supports, which are specific or non-specific for the one or more species of interest. This bringing into contact can be carried out directly in the outlet orifice containing the decomplexified sample. Capture supports which are functionalized for the specific or non-specific capture of the analytes sought and which can be used are, for example, and in a non-limiting manner: magnetic capture supports (magnetic microparticles or nanoparticles), porous or fibrous materials, latex beads, (ion, hydrophilic, hydrophobic, etc., exchange) resins. Advantageously, these supports can consist of one of the surfaces, in particular the horizontal or vertical surfaces of the decomplexified biological sample outlet orifice, said surface being functionalized.

This capture step makes it possible in particular to separate the pathogenic agents from the intrinsic flora present in the decomplexified sample. Since the decomplexified sample is freed of most of the non-specific particles initially present, such as food debris and non-soluble inhibitors such as fatty particles, the yield of this capture step is particularly improved.

Alternatively, this specific capture step can be carried out on dielectrophoresis (DEP) electrodes deposited on the surface of the device at the level of the outlet orifice. These electrodes can be either functionalized with capture antigens in the case of a capture on a panel of species being sought, or non-functionalized, when using only the well-known properties of capture by charge of the DEP technique. The identification can in both specific cases be confirmed or performed for example, by Raman or FTIR identification. Alternatively, this generic capture step, without antigens, using DEP can be reversible in order to release the microorganisms into a reduced volume (approximately 20 μl) allowing a step of identification by mass spectrometry, such as by MALDI-TOF mass spectrometry.

Preferentially, the treatment method as described above can comprise carrying out a step of enrichment of the biological sample, preferentially by incubation in the presence of a culture medium, before the introduction of said biological sample into the acoustophoresis device, and carrying out a lysis step following the separation step or following the capture step on a magnetic capture support. This lysis step makes it possible in particular to gain access to the biological information contained in the one or more species of interest. The term "biological information" is intended to mean any element constituting said species of interest or produced by the latter, such as nucleic acids (DNA, RNA), proteins, peptides or metabolites.

Advantageously, this lysis step can be followed by a step of extraction, amplification and analysis of the lysed sample, preferentially by quantitative PCR. The nucleic acids obtained at the end of the lysis step are thus detected and/or identified and/or quantified by any suitable genetic analysis method, for example by quantitative PCR (qPCR). The yield of these extraction, amplification and analysis steps is particularly improved by the step of separation of acoustophoresis, the latter making it possible in particular to remove a part of the amplification inhibitors.

Alternatively and following the separation step or the specific capture step, the treatment method according to the invention may comprise carrying out a step of analysis of the one or more species of interest separated and/or captured. This analysis step is preferentially an identification step, preferentially by plating out on a culture medium. Specific or non-specific culture media can be used for this analysis step. Preferentially, selective media such as chromogenic media can be used. The advantage of combining this type of analysis with a step of separation by acoustophoresis is that of being able to have a decomplexified sample that can be directly used to inoculate the culture medium. The inoculation of the culture medium can be carried out without any intermediate step, by taking the decomplexified sample from an outlet orifice of the device. Following the analysis step, the microorganism(s) contained in the biological sample can be detected and/or identified.

Alternatively, this analysis step is carried out by means of one or more immunoassay(s) specific for the one or more species of interest captured. This analysis step makes it possible, for example, to detect and/or identify and/or quantify the proteins and/or the metabolites of interest, initially present in the biological sample. These immunoassays can in particular be specific for the capture supports used in the capture step and allow their detection by means of a fluorescent or enzymatic label. Immunoassays and labels which can be used are, for example and in a nonlimiting manner: proteins specific for the microorganism(s) sought.

Alternatively and following the step of separation by acoustophoresis, the treatment method according to the invention can comprise carrying out a step of labeling with a fluorescent label which is non-specific or specific for the one or more species of interest.

By way of example of fluorescent labels, mention may be made of: labels for nucleic acids, such as propidium iodide, SYTO9 or else SYBR® Green, labels for membrane potential, such as DiBAC or else fluorescein derivatives coupled to enzymes specific for the microorganisms of interest, which, once cleaved inside the microorganism, become fluorescent.

By way of example, other labels can be used from the list below:
labels for nucleic acids: TOTO-3, SYTOX Green, Ethidium Bromide, Hoechst 33258/33342, SYTO 13, Mithramycin, Pyronin Y,
protein labels: FITC, Texas Red (sulforhodamine isothiocyanate), Oregon Green isothiocyanate,
cell function labels: Indo-1, Fura-2, Fluor-3,
pH-dependent labels: BCECF, SNARF-1, DIOC6(3),
labels for membrane potential: Oxonol, [DiBAC4(3)], Rhodamine 123, Fun-1,
lipophilic labels: Nile Red,
lectins coupled to fluorescent labels,
oligonucleotides coupled to fluorescent labels,
substrates coupled to fluorochromes,
antibodies coupled to fluorochromes.

This labeling step can be carried out on line, directly following the separation step, by bringing the decomplexified sample into contact with a solution containing fluorescent labels. This bringing into contact can be carried out directly in the outlet orifice containing the decomplexified sample.

Following this labeling step, the treatment method according to the invention can comprise carrying out a flow cytometry analysis step aiming to detect the presence of said fluorescent label. This step is preferentially carried out on line, directly following the labeling step. This step can be carried out by taking the decomplexified sample from the outlet orifice and by introducing it into a flow cytometer or by directly conveying it via a microfluidic device. Advantageously, the buffer solution introduced into the device for carrying out the step of separation by acoustophoresis can be compatible with a flow cytometry analysis step. Preferentially, this buffer solution can comprise fluorescent labels in order to directly carry out the labeling of the species of interest or of the intrinsic flora contained in the biological sample.

The term "biological sample" is intended to mean a liquid or viscous sample of food origin which contains an intrinsic flora and which may contain one or more species of interest, in particular microorganisms of interest, more particularly one or more pathogenic agent(s). A biological sample can have a solid or semi-solid matrix, in suspension in a liquid. By way of example of sample of food origin, mention may be made of meat samples (chicken, beef, minced beef, etc.), ready-cooked dishes, sauces, milk, fruit juice, rinsing liquid from carcasses, etc. Chicken samples are known for being particularly complex to treat, in particular the parts containing chicken skin, such as wings, legs, breasts and the skin of the neck.

Within the meaning of the present invention, the term "microorganism" covers Gram-positive or Gram-negative bacteria, yeasts, molds, amebae and more generally single-cell organisms, invisible to the naked eye, which can be handled and multiplied in the laboratory.

According to one preferred embodiment of the invention, the microorganism is a Gram-negative or Gram-positive bacterium, a yeast or a mold.

By way of example of Gram-positive bacteria, mention may be made of bacteria of the following genera: *Enterococcus, Streptococcus, Lactobacillus, Bifidobacterium, Staphylococcus, Bacillus, Listeria, Clostridium, Mycobacteria, Nocardia, Corynebacteria, Micrococcus* and *Deinococcus*.

By way of example of Gram-negative bacteria, mention may be made of bacteria of the following genera:

*Escherichia*, in particular *Escherichia coli* O157:H7, *Enterobacter, Klebsiella, Salmonella, Proteus, Serratia* and *Campylobacter*.

By way of example of yeasts, mention may be made of the following genera: *Candida, Cryptococcus, Saccharomyces* and *Trichosporon*.

By way of example of molds, mention may be made of the following genera: *Aspergillus, Penicillium, Cladosporium*.

The present invention also relates to various associated microfluidic devices which allow the decomplexification of food samples, thus allowing the capture and/or analysis of microorganisms that are contained or may be contained in the sample.

The present invention also relates to various supports for associated microfluidic devices which allow the decomplexification of food samples, thus allowing the capture and/or analysis of microorganisms that are contained or may be contained in the sample.

The present invention also relates to various connection devices or connectors for associated microfluidic devices which allow the decomplexification of food samples, thus allowing the capture and/or analysis of microorganisms that are contained or may be contained in the sample.

Finally, the present invention relates to an air regulation system which can be combined with connection devices or connectors for associated microfluidic devices which allow the decomplexification of food samples, thus allowing the capture and/or analysis of microorganisms that are contained or may be contained in the sample.

BRIEF DESCRIPTION OF THE DRAWINGS

The invention, its functionality, its applications and also its advantages will be understood more clearly on reading the present detailed description which follows, given with reference to the figures, in which:

FIG. 4 represents a view from above of a first microfluidic device with two inlet orifices according to the invention, capable of carrying out the process according to the invention, FIG. 5*a* represents a view along section B-B of the microfluidic device according to FIG. 4, FIG. 11 represents a view from above of a fifth microfluidic device with two inlet orifices according to the invention, capable of carrying out the process according to the invention, FIG. 12*a* represents a partial section along the plane A-A of FIG. 11, FIG. 12b represent a partial section along plane B-B of FIG. 11, FIG. 13a represents a connection device according to the invention viewed from above, FIG. 13b represents the connection device along the section A-A of FIG. 13a, FIG. 14 represents a diagrammatic view of an air regulation system which allows a method according to the present invention to be carried out and also a connection device according to the invention.

DETAILED DESCRIPTION

Figure 1:
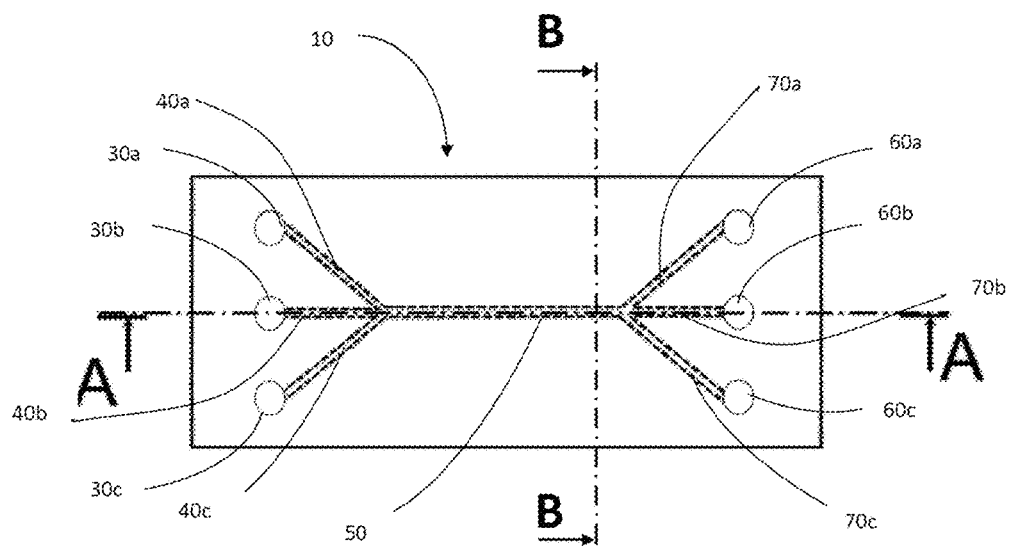
FIG. 1 represents a view from above of a microfluidic device of the prior art, capable of carrying out the process according to the invention.

The aim of the detailed description hereinafter is to disclose the invention in a sufficiently clear and complete manner, in particular with reference to the abovementioned figures, but should not in any case be regarded as limiting the extent of the protection to the particular embodiments which are the subjects of said figures.

Processes for preparing complex biological or chemical samples call for operations to separate the particles, cells or molecules in order to make possible or facilitate the analysis of particles, cells or molecules of interest, which may be contained in the sample. An objective of these sample preparation processes is thus to separate and/or concentrate the particles, cells or molecules of interest with respect to non-specific elements in order to enable, for example, their capture and/or detection.

Among the conventional processes for separating particles, centrifugation, filtration, chromatography or electrophoresis are very widely used for the preparation of complex biological or chemical samples. However, these methods are often painstaking to implement and do not make it possible to treat large volumes of samples. For example, filtration processes make it necessary to treat a defined volume of sample and then to perform a filter cleaning operation in order to prevent any blockage. This technique does not therefore make it possible to treat a complex biological or chemical sample in continuous flow. Furthermore, conventional techniques for preparing a biological sample, in particular chemical lysis or selective lysis, do not make it possible to ensure or can limit the viability of live cells such as bacteria following the preparation of the sample, and can thus have an impact on the quality of the subsequent capture, regrowth and/or detection steps.

Processes for separating particles, cells or molecules in continuous flow using microfluidic devices can make it possible to treat large volumes of sample, this being by continually introducing the sample into the microfluidic device. Another advantage of these techniques is their potential to be integrated upstream or downstream of a step of capture or analysis of the sample, thus performing a routing role and/or acting as a filter in a system for treatment and analysis of a complex biological or chemical sample.

A certain number of forces have been successfully used in microfluidic devices, including inertia, electric and magnetic forces and also mechanical contact forces. Among these various forces applied for separating particles, cells or molecules in microfluidic devices, acoustic forces generated from ultrasonic waves have also been widely used for separating particles of micrometric size in suspension, in order to separate them from their medium and/or other particles. This technique, termed acoustophoresis, enables non-destructive and label-free separation, solely on the basis of the size, the density and the compressibility of particles, cells or molecules.

Acoustophoresis consists of the application of a standing acoustic wave to one or more channels of a microfluidic device, which thus exhibits a pressure profile that is immobile and arranged transversely with respect to the targeted channel. The pressure profile of the standing acoustic waves applied thus varies between high-pressure zones called nodes and low-pressure zones called antinodes.

Conventionally, several fluids of identical densities are introduced, via conveying channels, into a microfluidic device so as to flow in laminar fashion (thus without mixing) in the separation channel, facing a piezoelectric ultrasonic transducer. When the transducer is not excited by a control signal, the fluids introduced escape from the separation channel without observing mixing or migration from one fluid to the other. By applying a control signal to the transducer, the particles present in the various fluids will be subjected to the acoustic force thus generated and will move toward the pressure nodes or the antinodes depending on their size, their density and their compressibility. The acoustic force is also called acoustic radiation pressure. The density of the fluids introduced and also their compressibility also have an influence. This migration of the particles in the separation channel thus makes it possible to promote their concentration in certain conveying channels and toward the outlet orifices of the microfluidic device, downstream of the separation channel.

The amplitude of the acoustic radiation generated by the transducer is proportional to that of the control signal applied; however, the maximum effects of the acoustic force are obtained from one and the same control signal when the frequency and the amplitude thereof cause the microfluidic device to resonate. For a configuration with a single pressure node, this resonance frequency is dependent on the width of the separation channel and also on the material of which the device is made. Conventional materials that can be used are glass or silicon, said materials having ideal surfaces for reflecting acoustic waves.

The radiation pressure due to the acoustic wave has a major influence on particles greater than 2 µm in size. Since this pressure is directly proportional to the volume of the particles, a minor change in the radius of the particle rapidly decreases or increases its impact thereon.

Another force is also created by a standing ultrasonic wave in a channel containing a suspension of microparticles. This force is due to the scattering and reflection of the acoustic wave in the fluid and on the particles. The acoustic scattering force is relatively weak and affects especially particles smaller than 2 μm.

An acoustophoresis separation device can thus be created by the use of an ultrasonic acoustic transducer facing a surface of reflection or a second transducer so as to establish a resonant standing wave in the separation channel.

A microfluidic device thus comprises at least two inlet orifices, a separation channel and at least two outlet orifices. The inlet orifices open to the separation channel, while the separation channel opens to the outlet orifices. The device is arranged such that an ultrasonic transducer can be integrated into or attached to a wall of said separation channel. The ultrasonic transducer thus integrated or attached is capable of transmitting mechanical oscillations in multiple acoustic waves acting on the content of the separation channel.

Figure 2A:
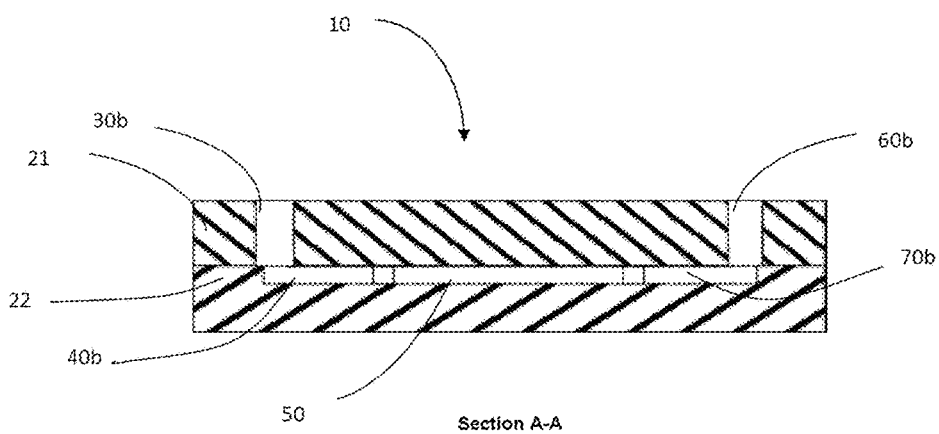
FIG. 2*a* represents a view in longitudinal section of the microfluidic device of the prior art according to the plane of section A-A of FIG. 1.

As represented in FIGS. 1 and 2a, a microfluidic device 10 of the prior art comprises two fluidic parts 21, also called cover plate, and 22, also called separator. The separator and the cover plate are substantially flat, and assembled together so as to form fluidic channels. The separator is linked to the cover plate so as to produce a device 10 that can be observed by an optical analysis device such as a microscope.

The device is composed of three inlet orifices 30a, 30b, 30c and of three outlet orifices 60a, 60b and 60c connected by a rectilinear separation channel 50, which is 35 mm in length, allowing, during operation of the system, the cells, particles or molecules to become acoustically concentrated in the conveying channel 70b, the axis of which is identical to and in the extension of the axis of the separation channel 50. The cells, particles or molecules are acoustically concentrated in the central channel according to their density, their size and their compressibility.

The three inlet orifices 30a, 30b, 30c, communicate with the separation channel 50 by means of conveying channels respectively 40a, 40b, 40c. The separation channel 50 also communicates with the three outlet orifices 60a, 60b, 60c, by means of conveying channels, respectively 70a, 70b, 70c.

The separator 22 comprises a glass plate 1 mm thick, coated with a layer of chromium and with a layer of photosensitive resin. After development of the photosensitive layer, the glass is etched with hydrofluoric acid (HF) producing conveying and separation channels 125 μm deep, having a width, at the bottom of the channels, of less than 375 μm, and a width of greater than 625 μm in the plane of the separator in contact with the cover plate. The cover plate 21 is pierced so as to produce the inlet and outlet orifices and then thermally bonded with the separator in order to produce a sealed assembly.

The conveying channels of the inlet orifices 40a, 40b, 40c have an angle of respectively 45°, 0° and minus 45° relative to the separation channel in the plane of the separator, so as to slow down the flow rate of the fluids from the conveying channels having an angle of 45° or −45°, 40a, 40c, relative to the separation channel, and to thus promote the appearance of a laminar flow in the separation channel.

Figure 2B:
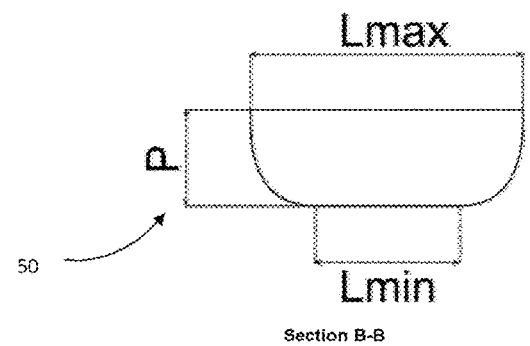
FIG. 2*b* represents a cross section of the separation channel 50 according to the plane of section B-B of FIG. 1.

The standard profile of a conveying or separation channel is represented in FIG. 2b. The channels are D-shaped in the plane perpendicular to the axis of the channel in question, the greatest width being located in the plane in contact with the cover plate when the device is assembled. They thus have a lower width "Lmin" at the bottom of the channels, an upper width "Lmax" in the plane of the separator in contact with the cover plate when the device is assembled, and also a depth P.

This device of the prior art is capable of carrying out processes for preparing biological samples by acoustophoresis such as the process of the invention. For this, all or part of the biological sample to be treated is introduced into the inlet orifices 30a and 30c of the device 10. A buffer solution is introduced into the inlet orifice 30b, the buffer and the sample being introduced at respective flow rates capable of generating a laminar flow in the separation channel. An ultrasonic transducer, such as a piezoelectric transducer, attached to the separation channel is then activated by a control signal, so as to carry out a step of separation of said biological sample by acoustophoresis. This separation makes it possible to promote the concentration of the non-specific particles, such as food debris, present in the sample, in the outlet orifice 60b of said acoustophoresis device. The decomplexified sample is obtained in the outlet orifices 60a and 60c.

The invention also relates to various microfluidic devices which allow the treatment of biological samples by acoustophoresis. These various devices are also capable of advantageously carrying out the process according to the invention. These devices are particularly advantageous to use with the process according to the invention since they make it possible to achieve sample treatment flow rates which are higher than prior art devices while at the same time ensuring a degree of decomplexification which is equal to or greater than those observed in the prior art for biological samples such as food samples. Furthermore, these devices according to the invention make it possible to treat a large variety of food samples, the size of their channels, in particular their separation channels, being optimized for the different sizes of non-specific particles or debris which may be observed.

The inlet orifices and the shape of the conveying channels communicating with the inlet orifices can advantageously be optimized in order to accept a sedimentation of the non-specific particles or debris at the inlets of the microfluidic device without risk of blocking the channels of the device. In this respect, the part of each conveying channel opposite each inlet orifice capable of receiving the biological sample can have a cavity with a depth greater than the general depth of the conveying channel. Advantageously, the cavity opposite the inlet orifice is two to three times deeper than the conveying channel connected to said orifice. This cavity makes it possible to create a zone of slowed or zero speed of the sample introduced, promoting sedimentation of the non-specific particles. The device thus formed exhibits better tolerance to blockages linked to the introduction of debris of large size and high density.

For each of these embodiments, the separator can be made of silicon, ceramic or glass, the channels being obtained by chemical or physical etching (e.g. sanding). The separator can also be made of flexible and thin polymer material such as polydimethylsiloxane (PDMS), polypropylene or a polymer/silicone bicompound (for example a polystyrene with a flexible film of silicone or of PDMS in order to ensure air-free coupling of the piezoelectric transducers on the wall of the device), the channels then being obtained by molding. The advantage of the use of a flexible and thin polymer material is to be able to produce a device at very low cost, allowing its routine use as a consumable in processes for preparing biological samples by acoustophoresis such as the process according to the invention. Another advantage is that of not requiring any adhesive or coupling gel between the piezoelectric transducer(s) and the walls of the separation channel.

For each of these embodiments, each inlet or outlet orifice can form a reservoir so as to be able to carry out sample storage operations and also depositing or pipetting operations. A step of incubation of the sample can also be carried out by attaching a heating means at an orifice. Advantageously, an orifice can be made in a transparent or translucent material, so as to be able to directly carry out a reading of the optical density of the sample that it contains.

For each of these embodiments, each device can be used alone or in parallel so as to be able to treat the same volume of biological sample at a higher flow rate. Indeed, if the flow rate of introducing the fluids into one and the same separation channel is increased, the degree of decomplexification of the sample can rapidly decrease, since the particles do not have time to be separated by the acoustic wave due to too short a residence time in the device. Furthermore, if the size of the channels, in particular of the separation channel, is increased, in the hope of also being able to increase the treatment flow rate, the amplitude of excitation (of the control signal) of the piezoelectric transducer(s) required for good separation of the particles will have to be much greater since the resonance frequency will be reduced and consequently the radiation pressure on the particles to be focused at the center of the separation channel. However, if the ultrasonic transducer is excited at a greater amplitude, it can cause local heating in the separation channel. This heating is not desirable since it can cause degradation of the device and also of the viability of the particles, cells or molecules of interest present in the separation channel. Furthermore, this heating can cause a change in density of the buffer used, which can modify the propagation of the acoustic waves in the channel and disrupt the separation step. As a result, the devices according to the invention, used alone or in parallel, make it possible to obtain separation/decomplexification flow rates that are equal to or greater than the prior art while at the same time guaranteeing the viability of the particles, cells or molecules of interest treated.

Thus, the separation channels of the various devices according to the invention have a length that can be between 35 mm and 80 mm. The lower widths of the separation channel are for example between 300 µm and 375 µm, the upper widths are for example between 550 µm and 625 µm. The depth of the separation channel can be between 100 µm and 150 µm, preferentially 125 µm. The various devices according to the invention are suitable for use with control signals of attached ultrasonic transducer(s) having a frequency of between 300 kHz and 10 MHz, preferentially of 1.3 MHz, alternatively of 1.44 MHz for the creation of a single pressure node at the center of the channel. These various frequency values make it possible to obtain central focusing (a single pressure node in the separation channel) exhibiting non-specific particles focused in the outlet orifice in the extension of the axis of the separation channel or to promote the concentration of these non-specific particles in one of the outlet orifices. Various resonance frequencies can be observed for one and the same device due to the appearance of several pressure nodes in the width of the separation channel in multiples of a quarter of the wavelength (nλ/4). Slight variations of approximately 30 kHz around the resonance frequency can also make it possible to obtain better resonance of the device, this frequency being dependent on the quality of production of the channels of the device.

The amplitude of the control signal is between 0.1 V and 100 V, preferentially 38 V. For control signal amplitudes greater than 38 V, it may be desirable to use a cooling device attached to the ultrasonic transducer(s) in order to prevent degradation of the device and/or damage to the viability of the particles, cells or molecules present in the separation channel. Peltier blocks or fans can constitute such cooling devices. Advantageously, the cooling device is temperature-controlled in order to regulate the temperature in the vicinity of the ultrasonic transducer.

For each of these embodiments, the conveying channels of the inlet orifices used to introduce the biological sample have an angle of between 30 and 60°, preferentially of 45° relative to the separation channel in the plane of the separator. This angle can easily be adjusted by those skilled in the art so as to more or less slow down the flow rate of introduction of the fluid into the separation channel, and to thus ensure the appearance of a laminar flow of the fluids in this channel. These conveying channels are called side channels since they make it possible to introduce the fluid in the direction of the walls of the separation channel.

For each of these embodiments, the conveying channels to the outlet orifices used to recover or reintroduce the decomplexified sample have an angle of between 30 and 60°, preferentially of 45° relative to the separation channel in the plane of the separator. This angle can easily be adjusted by those skilled in the art so as to more or less slow down the flow rate of suction of the fluid out of the separation channel, and to thus ensure the appearance of a laminar flow of the fluids in this channel. These conveying channels are also called side channels since they make it possible to suction the fluid circulating along the walls of the separation channel.

The conveying channels of which the axis or axes is or are identical to the axis of the separation channel are called central channels. These channels transport the concentrated sample.

Furthermore, the cross sections of the conveying channels of the inlet and outlet orifices can be adjusted. In particular, the cross sections of the conveying channels of the side outlet orifices (in which the decomplexified sample is found) relative to the cross section of the conveying channel of the central outlet orifice (in which a maximum of non-specific particles is found) can be adjusted in order to guarantee better focusing at the level of the outlet branching between these channels. In this zone, at the junction of the separation channel and the conveying channels to the outlet orifices, the resonance is not very effective (since there are no longer side walls at the branching) for a short transient time. This results in a partial loss of focusing of the non-specific particles. In the case of the device illustrated in FIG. 1, the adjustment of the ratios of the cross sections between the channels 70a or 70c and 70b can thus make it possible to minimize the losses of microorganisms or to improve the degree of concentration of the non-specific particles or debris in the central conveying channel 70b.

A first embodiment of a device according to the invention is represented in FIGS. 4 and 5a. This device 200 comprises two inlet orifices 230a, 230b, a separation channel 250 and at least two outlet orifices 260a, 260b. The device 200 comprises two fluidic parts, a separator 222 and a cover plate 221, which are substantially planar. These two parts are assembled hermetically. The inlet orifices open to the separation channel, while the separation channel opens to the outlet orifices by means of conveying channels. Thus, the separation channel 250 opens to the orifice 230a via the conveying channel 240a, to the orifice 230b via the conveying channel 240b, to the orifice 260a via the conveying channel 270a, and to the orifice 260b via the conveying channel 270*b*. In a first alternative of implementation of this first embodiment, the device is arranged such that at least one ultrasonic transducer can be integrated into or attached to a wall of said separation channel. The ultrasonic transducer thus integrated or attached is capable of transmitting mechanical oscillations in multiple acoustic waves which can act on the content of the separation channel.

In a second alternative implementation of this first embodiment, the device comprises two recesses 290*a*, 290*b*, made along the separation channel 250, in the separator 222, and capable of each receiving an ultrasonic transducer. This embodiment makes it possible to obtain a standing wave in a separator made of a material that barely reflects acoustic waves, the material being flexible and thin such as plastic, polymer or silicone materials. A silicone preferentially used is polydimethylsiloxane (PDMS). Preferentially, each ultrasonic transducer comprises a quarter-wave adapter plate, the acoustic impedance of which is calculated to minimize the energy losses, and thus the heating, between the ultrasonic transducer and the walls of the device. This plate of resin covering the piezoelectric transducer(s) (made by casting and polymerization) is defined so as to have an intermediate acoustic impedance between the acoustic impedance of the material used to produce the device and the acoustic impedance of the piezoelectric transducer(s).

Preferentially, the cover plate 221 is made of polydimethylsiloxane (PDMS) or of molded plastic such as polycarbonate (PC) poly(methyl methacrylate) (PMMA), polypropylene (PP), polystyrene (PS), acrylonitrile butadiene styrene (ABS), cyclic olefin copolymer (COC), cyclic olefin polymer (COP) or polyoxymethylene (POM).

This device 200 is capable of carrying out processes for preparing biological samples by acoustophoresis such as the process according to the invention. For this, all or part of the biological sample to be treated is introduced into the inlet orifice 230*a* of the device 200. A buffer solution is introduced into the inlet orifice 230*b*, the buffer and the sample being introduced at respective flow rates capable of generating a laminar flow in the separation channel. An ultrasonic transducer, such as a piezoelectric transducer, attached to the separation channel is then activated by a control signal, so as to carry out a step of separation of said biological sample by acoustophoresis. This separation makes it possible to promote the concentration of the non-specific particles, such as food debris, present in the sample, in the outlet orifice 260*b* of said acoustophoresis device. The decomplexified sample is obtained in the outlet orifice 260*a*. The non-specific particles are thus transferred into the buffer solution introduced into the inlet 230*b*.

Figure 5B:
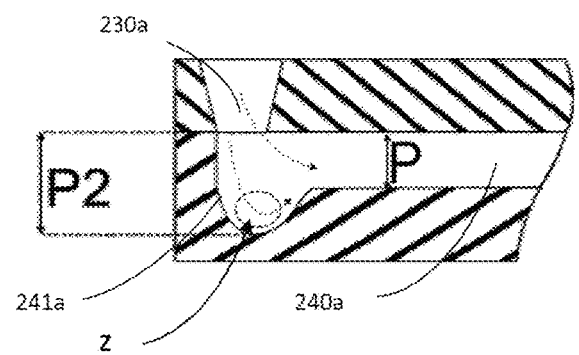
FIG. 5*b* represents one embodiment of an inlet orifice viewed along section A-A of an inlet orifice of the microfluidic device according to FIG. 4.

An alternative for producing the inlet orifice 230*a* is presented in FIG. 5*b*. The inlet orifice 230*a* in this case has a frustoconical shape but can also be cylindrical depending on the introduction means chosen. The shape of the conveying channel 240*a*, opposite the orifice 230*a*, is modified so as to comprise a cavity 241*a* of greater depth than the general depth of the conveying channel 240*a*. This cavity thus has a depth P2 with P2 between two and three times the depth P of the conveying channel. This cavity makes it possible to create a zone of slowed or zero speed (Z) of the sample introduced, promoting the sedimentation of the non-specific particles contained in the sample. The device thus formed exhibits better tolerance to blockages associated with the introduction of debris of large size and high density.

Figure 6A:
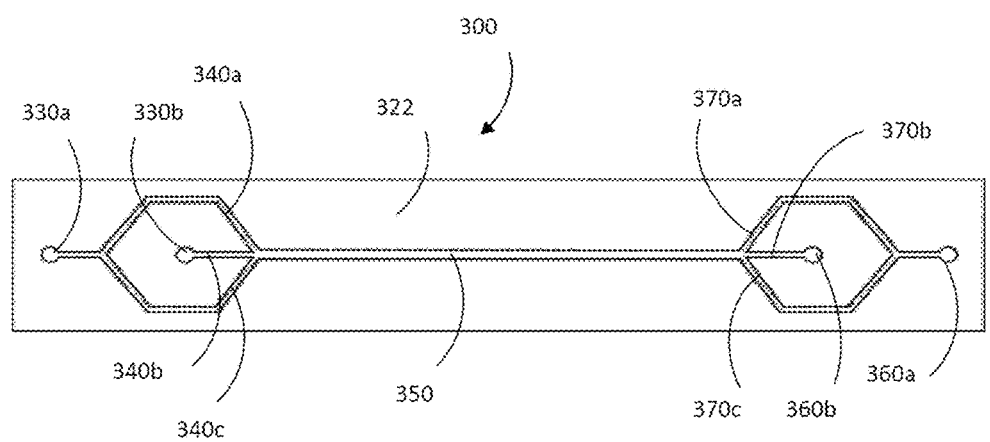
FIG. 6*a* represents a view from above of a second microfluidic device with two inlet orifices according to the invention, capable of carrying out the process according to the invention.

As represented in FIG. 6*a*, the invention also relates to a second embodiment of a device 300 comprising two fluidic parts, a separator 322 and a cover plate (not represented), these two parts being substantially planar. These two parts are assembled hermetically. Channels are made in the separator 322. The device 300 comprises two inlet orifices 330*a*, 330*b*, in fluidic communication with at least one separation channel 350 by means of conveying channels respectively 340*a*, 340*c* for the orifice 330*a* and 340*b* for the orifice 330*b*. The separation channel 350 is also in fluidic communication with two outlet orifices 360*a*, 360*b*, by means of conveying channels, respectively 370*a* and 370*c* for the orifice 360*a* and 370*b* for the orifice 360*b*. This configuration makes it possible to simplify the fluidic connection since it has only two inlet orifices and two outlet orifices. Likewise, the collection of the decomplexified sample can be carried out in an outlet orifice or a single collection tube. Furthermore, since the conveying channels 370*a* and 370*c* to the outlet orifice 360*a* are directly connected by etching of the channels on the device, the equilibration of the pressure drops at the branching of the conveying channels to the outlet orifices is significantly improved. A minimal difference in pressure drop (linked to a difference in connection of the outlet tubes on the device) can lead to a disruption of the focusing and thus considerable degradation of the decomplexification performance levels.

The device 300 is arranged such that an ultrasonic transducer, not represented, can be integrated into or attached to a wall of said separation channel 350. The ultrasonic transducer thus integrated or attached is capable of transmitting mechanical oscillations in multiple acoustic waves that can act on the content of the separation channel and generate therein a standing acoustic wave. An alternating current generator combined with a signal amplifier (which are not represented), can be electrically connected to the transducer in order to generate a signal for control of the transducer, the frequency, waveform and amplitude of which are known.

In one particular embodiment of the device 300, the separator 322 is made of a glass plate 1 mm thick, coated with a layer of chromium and with a layer of photosensitive resin. After development of the photosensitive layer, the glass is etched with hydrofluoric acid (HF). The conveying channels 340*a* and 340*c*, 370*a* and 370*c* have a depth P of 125 µm, a lower width Lmin, at the bottom of the channels, of 300 µm, and an upper width Lmax of 550 µm in the plane of the separator in contact with the cover plate. The conveying channels 340*b* and 370*b* and also the separation channel 350 have a depth P of 125 µm, a lower width Lmin, at the bottom of the channels, of 375 µm, and an upper width Lmax of 625 µm in the plane of the separator in contact with the cover plate. The cover plate is pierced so as to produce the inlet and outlet orifices and then thermally bonded with the separator in order to produce a sealed assembly. The conveying channels of the inlet orifices 340*a*, 340*b* have an angle of respectively 45°, 0° and minus 45° relative to the separation channel 350 in the plane of the separator, so as to slow down the flow rate of the fluids originating from the conveying channels having an angle of 45° or −45°, 340*a*, 340*c*, relative to the separation channel. The rectilinear separation channel 350 has a length of 80 mm, allowing the cells, particles or molecules to become acoustically concentrated in the conveying channel 370*b* during the operation of the system. The axis of the conveying channel 370*b* is identical to the axis of the separation channel. The cells, particles or molecules are acoustically concentrated in the central channel 370*b*, according to their density, their size and their compressibility.

Alternatively, the separator 322 of the device 300 comprises two recesses (not represented) made along the separation channel 350, and capable of each receiving an ultrasonic transducer (not represented). This embodiment makes it possible to obtain a standing wave in the separator 322 if the latter is made of a material that does not reflect acoustic waves very much, the material being flexible and thin such as plastic, polymer or silicone materials. A silicone preferentially used is polydimethylsiloxane (PDMS). Preferentially, each ultrasonic transducer comprises a quarter-wave adapter plate of which the acoustic impedance is calculated to minimize the energy losses, and thus the heating, between the ultrasonic transducer and the walls of the device.

Preferentially, the cover plate (not represented) is made of PDMS or of molded plastic such as polycarbonate (PC), poly(methyl methacrylate) (PMMA), polypropylene (PP), polystyrene (PS), acrylonitrile butadiene styrene (ABS), cyclic olefin copolymer (COC), cyclic olefin polymer (COP) or polyoxymethylene (POM).

This device 300 is capable of carrying out processes for preparing biological samples by acoustophoresis such as the process according to the invention. For this, all or part of the biological sample to be treated is introduced into the inlet orifice 330a of the device 300. A buffer solution is introduced into the inlet orifice 330b, the buffer and the sample being introduced at respective flow rates capable of generating a laminar flow in the separation channel. An ultrasonic transducer, such as a piezoelectric transducer, attached to the separation channel is then activated by a control signal, so as to carry out a step of separation of said biological sample by acoustophoresis. This separation makes it possible to promote the concentration of the non-specific particles, such as food debris, present in the sample, in the outlet orifice 360b of said acoustophoresis device. The decomplexified sample is obtained in the outlet orifice 360a.

Figure 6B:
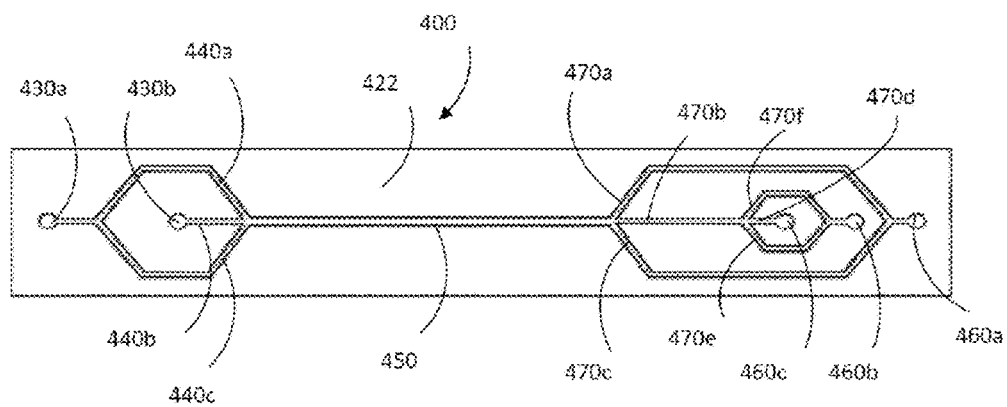
FIG. 6*b* represents a view from above of a third microfluidic device with two inlet orifices according to the invention, capable of carrying out the process according to the invention.

As represented in FIG. 6b, the invention also relates to a third device 400 comprising two fluidic parts, a separator 422 and a cover plate (not represented), these two parts being substantially planar. These two parts are assembled hermetically. Fluidic channels are made in the separator 422. The device 400 comprises two inlet orifices 430a, 430b, in fluidic communication with at least one separation channel 450 by means of conveying channels, respectively 440a, 440c, for the orifice 430a and 440b for the orifice 430b. The separation channel 450 is also in fluidic communication with three outlet orifices 460a, 460b, 460c, by means of conveying channels, respectively 470a and 470c for the orifice 460a, 470b and 470d for the orifice 460c, and 470b, 470f and 470e for the outlet orifice 460b. The device 400 is arranged such that an ultrasonic transducer, not represented, can be integrated into or attached to a wall of said separation channel 450. The ultrasonic transducer thus integrated or attached is capable of transmitting mechanical oscillations in multiple acoustic waves that can act on the content of the separation channel and generate therein a standing acoustic wave. A function generator combined with a signal amplifier, which are not represented, can be electrically connected to the transducer in order to generate a transducer control signal of which the frequency, the waveform and the amplitude are known. The conveying channel 470b, placed in the extension of the separation channel 450, makes it possible to carry out a second step of separation of the non-specific particles that may remain in the biological sample.

In one particular embodiment of the device 400, the separator 422 is made of a glass plate 1 mm thick, coated with a layer of chromium and with a layer of photosensitive resin. After development of the photosensitive layer, the glass is etched with hydrofluoric acid (HF). The conveying channels 440a, 440c, 470a, 470c, 470e and 470f have a depth P of 125 µm, a lower width Lmin, at the bottom of the channels, of 300 µm, and an upper width Lmax of 550 µm in the plane of the separator in contact with the cover plate. The conveying channels 440b, 470b and 470d and also the separation channel 450 have a depth P of 125 µm, a lower width Lmin, at the bottom of the channels, of 375 µm, and an upper width Lmax of 625 µm in the plane of the separator in contact with the cover plate. The cover plate is pierced so as to make the inlet and outlet orifices and then thermally bonded with the separator in order to produce a sealed assembly. The conveying channels of the inlet orifices 440a, 440b, 440c have an angle of respectively 45°, 0° and minus 45° relative to the separation channel 450 in the plane of the separator, so as to slow down the flow rate of the fluids originating from the conveying channels having an angle of 45° or −45°, 440a, 440c, relative to the separation channel. The rectilinear separation channel 450 has a length of 80 mm, making it possible, during operation of the system, for the cells, particles or molecules to become acoustically concentrated in the conveying channel 470b then 470d, the axes of which are identical to the axis of the separation channel.

Alternatively, the separator 422 of the device 400 comprises two recesses (not represented) made along the separation channel 450 and capable of each receiving an ultrasonic transducer (not represented). This embodiment makes it possible to obtain a standing wave in the separator 422 if the latter is made of a material which does not reflect acoustic waves very much, the material being flexible and thin such as plastic, polymer or silicone materials. A silicone preferentially used is polydimethylsiloxane (PDMS). Preferentially, each ultrasonic transducer comprises a quarter-wave adapter plate of which the acoustic impedance is calculated so as to minimize the energy losses, and thus the heating, between the ultrasonic transducer and the walls of the device.

Preferentially, the cover plate (not represented) is made of PDMS or of molded plastic such as polycarbonate (PC), poly(methyl methacrylate) (PMMA), polypropylene (PP), polystyrene (PS), acrylonitrile butadiene styrene (ABS), cyclic olefin copolymer (COC), cyclic olefin polymer (COP) or polyoxymethylene (POM).

This device 400 is capable of carrying out the processes for preparing biological samples by acoustophoresis such as the process according to the invention. For this, all or part of the biological sample to be treated is introduced into the inlet orifice 430a of the device 400. A buffer solution is introduced into the inlet orifice 430b, the buffer and the sample being introduced at respective flow rates capable of generating a laminar flow in the separation channel. An ultrasonic transducer, such as a piezoelectric transducer, attached to the separation channel is then activated by a control signal, so as to carry out a step of separation of said biological sample by acoustophoresis. This separation makes it possible to promote the concentration of the non-specific particles, such as food debris, present in the sample, in the conveying channel 470b of said acoustophoresis device. The decomplexified sample is obtained in the outlet orifice 460a. A second step of separation of said biological sample by acoustophoresis is carried out on the part resulting in the first separation in the channel 470b. This separation makes it possible to promote the concentration of the non-specific particles, such as food debris, present in the sample, in the outlet orifice 460c of said acoustophoresis device. The sample decomplexified a second time is obtained in the outlet orifice 460b. The collection and the mixing of the decomplexified samples from the outlet orifices 460a and 460b make it possible to increase the collection yield of the microorganisms present in the biological sample. This is because the microorganisms entrained with the non-specific particles during the first separation in the channel 470b are capable of being separated by acoustophoresis in this channel 470b and of thus being capable of being collected following this second separation in the orifice 460b.

The relative position and the length of the second separation channel 470b with respect to the main separation channel 450 is chosen according to the desired applications, performance levels and flow rates.

Figure 6C:
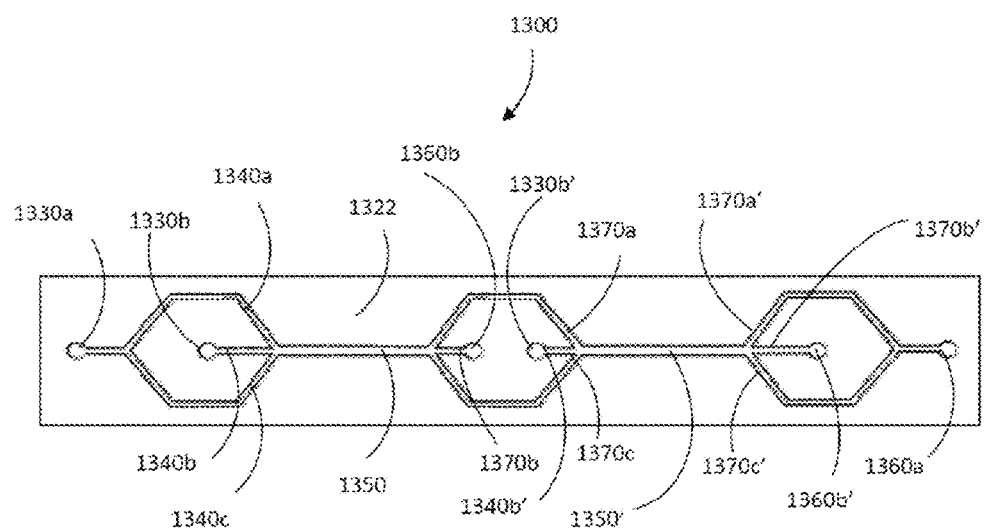
FIG. 6*c* represents a view from above of a fourth microfluidic device with three inlet orifices according to the invention, capable of carrying out the process according to the invention.

As represented in FIG. 6c, the invention also relates to a fourth embodiment of a device 1300 comprising two fluidic parts, a separator 1322 and a cover plate (not represented), these two parts being substantially planar. These two parts are assembled hermetically. Channels are made in the separator 1322. The device 1300 comprises two inlet orifices 1330a, 1330b, in fluidic communication with a first separation channel 1350 by means of conveying channels, respectively 1340a, 1340c for the orifice 1330a and 1340b for the orifice 1330b. The separation channel 1350 is in fluidic communication with an outlet orifice 1360b, by means of a conveying channel 1370b. The separation channel 1350 is also in fluidic communication with a second separation channel 1350' by means of two conveying channels 1370a and 1370c. The second separation channel 1350' is in fluidic communication with an outlet orifice 1360b', by means of a conveying channel 1370b' and in fluidic communication with an outlet orifice 1360a, by means of two conveying channels 1370a' and 1370c'.

The device 1300 also comprises an inlet orifice 1330b', in fluidic communication with the second separation channel 1350' via a conveying channel 1340b'.

The device 1300 is arranged such that one or more ultrasonic transducers, not represented, can be integrated into or attached to a wall of said separation channels 1350 and 1350'. The ultrasonic transducer(s) thus integrated or attached is (are) capable of transmitting mechanical oscillations in multiple acoustic waves that can act on the content of the separation channels and generate therein a standing acoustic wave. An alternating current generator combined with a signal amplifier, which are not represented, can be electrically connected to the transducer(s) in order to generate a control signal of which the frequency, the waveform and the amplitude are known.

This configuration makes it possible to improve the purity of the decomplexified sample. Indeed, after having concentrated the non-specific particles toward the outlet orifice 1360b, the decomplexified sample is injected into the second separation channel 1350' via the channels 1370a and 1370c. The decomplexified sample is then separated a second time from the non-specific particles that may still be present, said particles being in the orifice 1360b'. The sample decomplexified a second time is obtained in the outlet orifice 1360a.

In one particular embodiment of the device 1300, the separator 1322 is made of a glass plate 1 mm thick, coated with a layer of chromium and with a layer of photosensitive resin. After development of the photosensitive layer, the glass is etched with hydrofluoric acid (HF). The conveying channels 1340a and 1340c, 1370a, 1370c, 1370a' and 1370c' have a depth P of 125 µm, a lower width Lmin, at the bottom of the channels, of 300 µm, and an upper width Lmax of 550 µm in the plane of the separator in contact with the cover plate. The conveying channels 1340b, 1340b', 1370b and 1370b' and also the separation channels 1350 and 1350' have a depth P of 125 µm, a lower width Lmin, at the bottom of the channels, of 375 µm, and an upper width Lmax of 625 µm in the plane of the separator in contact with the cover plate. The cover plate is pierced so as to make the inlet and outlet orifices and then thermally bonded with the separator in order to produce a sealed assembly.

The conveying channels of the inlet orifices 1340a, 1340b have an angle of respectively 45°, 0° and minus 45° relative to the separation channel 1350 in the plane of the separator, so as to slow down the flow rate of the fluids originating from the conveying channels having an angle of 45° or −45°, 1340a, 1340c, relative to the separation channel 1350. The rectilinear separation channel 1350 has a length of 19.5 mm, allowing the cells, particles or molecules to become acoustically concentrated in the conveying channel 1370b during operation of the system. The axis of the conveying channel 1370b is identical to the axis of the separation channel.

The conveying channels 1370a, 1370b, 1340b' have an angle of respectively 45°, 0° and minus 45° relative to the separation channel 1350' in the plane of the separator, so as to slow down the flow rate of the fluids originating from the conveying channels having an angle of 45° or −45°, 1340a, 1340c, relative to the second separation channel 1350'. The rectilinear second separation channel 1350' has length of 19.5 mm, allowing the cells, particles or molecules to become acoustically concentrated in the conveying channel 1370b' during operation of the system. The axis of the conveying channel 1370b' is identical to the axis of the separation channel 1350'. The cells, particles or molecules are acoustically concentrated in the central channel 1370b', according to their density, their size and the compressibility.

Alternatively, the separator 1322 of the device 1300 comprises four recesses (not represented) made along the separation channels 1350 and 1350', and capable of each receiving an ultrasonic transducer (which are not represented). This embodiment makes it possible to obtain a standing wave in the separator 1322 if the latter is made of a material which does not reflect acoustic waves very much, the material being flexible and thin such as plastic, polymer or silicone materials. A silicone preferentially used is polydimethylsiloxane (PDMS). Preferentially, each ultrasonic transducer comprises a quarter-wave adapter plate of which the acoustic impedance is calculated so as to minimize the energy losses, and thus the heating, between the ultrasonic transducer and the walls of the device.

Preferentially, the cover plate (not represented) is made of PDMS or of molded plastic such as polycarbonate (PC), poly(methyl methacrylate) (PMMA), polypropylene (PP), polystyrene (PS), acrylonitrile butadiene styrene (ABS), cyclic olefin copolymer (COC), cyclic olefin polymer (COP) or polyoxymethylene (POM).

This device 1300 is capable of carrying out processes for preparing biological samples by acoustophoresis such as the process according to the invention. For this, all or part of the biological sample to be treated is introduced into the inlet orifice 1330a of the device 1300. A buffer solution is introduced into the inlet orifices 1330b and 1330b', the buffers and the sample being introduced at respective flow rates capable of generating a laminar flow in the separation channels 1350 and 1350'. One or more ultrasonic transducer(s) attached to the separation channels is (are) then activated by a control signal, so as to carry out two successive steps of separation of said biological sample by acoustophoresis. This separation makes it possible to promote a first time the concentration of the non-specific particles, such as food debris, present in the sample, in the outlet orifice 1360b. Following this first separation, a second separation makes it possible to promote the concentration of the non-specific particles a second time, such as food debris still present in the decomplexified sample originating from the channels 1370a and 1370c, in the outlet orifice 1360b'. The sample decomplexified a second time and having an improved purity is obtained in the outlet orifice 1360a.

The relative position and the length of the second separation channel 1350' with respect to the main separation channel 1350' are chosen according to the desired applications, performance levels and flow rates. Advantageously, two buffer solutions of different type or density are introduced into the inlet orifices 1330b and 1330b'.

Figure 6D:
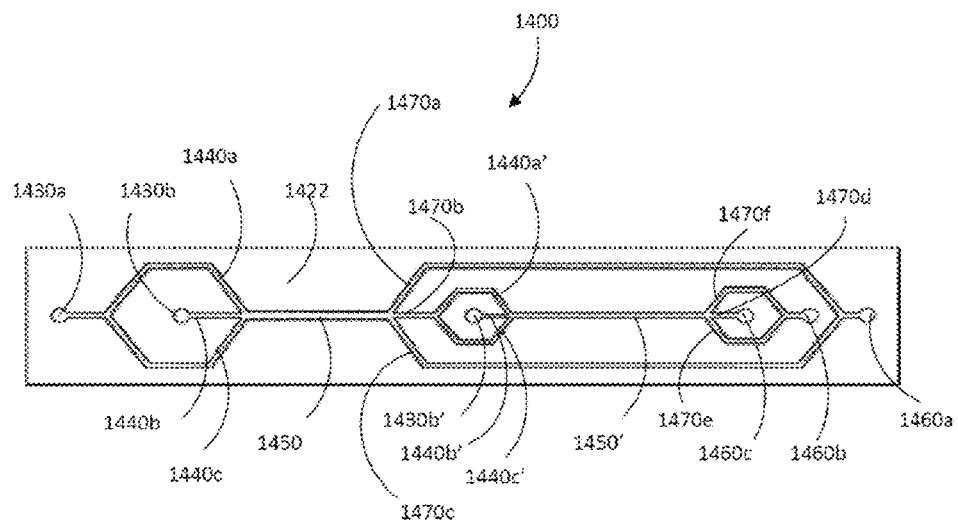
FIG. 6*d* represents a view from above of a fifth microfluidic device with three inlet orifices according to the invention, capable of carrying out the process according to the invention.

As represented in FIG. 6d, the invention also relates to a fifth device 1400 comprising two fluidic parts, a separator 1422 and a cover plate (not represented), these two parts being substantially planar. These two parts are assembled hermetically. Fluidic channels are made in the separator 1422. The device 1400 comprises two inlet orifices 1430a, 1430b, in fluidic communication with a first separation channel 1450 by means of conveying channels respectively 1440a, 1440c for the orifice 1430a and 1440b for the orifice 1430b.

The first separation channel 1450 is also in fluidic communication with an outlet orifice 1460a, by means of conveying channels 1470a and 1470c.

The first separation channel 1450 is finally in fluidic communication with the second separation channel 1450', by means of conveying channels 1440a' and 1440c'.

The device 1400 also comprises an inlet orifice 1430b', in fluidic communication with the second separation channel 1450 via the conveying channel 1440b'.

The second separation channel 1450' is also in fluidic communication with two outlet orifices 1460b, 1460c, by means of conveying channels, respectively 1470d for the orifice 1460c; 1470e and 1470f for the outlet orifice 1460b.

The device 1400 is arranged such that one or more ultrasonic transducer(s), not represented, can be integrated into or attached to a wall of said separation channels 1450 and 1450'. The ultrasonic transducer(s) thus integrated or attached is (are) capable of transmitting mechanical oscillations in multiple acoustic waves that can act on the content of the separation channels and generate therein a standing acoustic wave. An alternating current generator combined with a signal amplifier, not represented, can be electrically connected to the transducer(s) in order to generate a control signal of which the frequency, the waveform and the amplitude are known.

In one particular embodiment of the device 1400, the separator 1422 is made of a glass plate 1 mm thick, coated with a layer of chromium and with a layer of photosensitive resin. After development of the photosensitive layer, the glass is etched with hydrofluoric acid (HF). The conveying channels 1440a, 1440c, 1470a, 1470c, 1470e and 1470f have a depth P of 125 µm, a lower width Lmin, at the bottom of the channels, of 300 µm, and an upper width Lmax of 550 µm in the plane of the separator in contact with the cover plate. The conveying channels 1440b, 1470b and 1470d and also the separation channels 1450 and 1450' have a depth P of 125 µm, a lower width Lmin, at the bottom of the channels, of 375 µm, and an upper width Lmax of 625 µm in the plane of the separator in contact with the cover plate. The cover plate is pierced so as to make the inlet and outlet orifices and then thermally bonded with the separator in order to produce a sealed assembly. The conveying channels 1440a, 1440c have an angle of respectively 45° and minus 45° relative to the separation channel 1450 in the plane of the separator, so as to slow down the flow rate of the fluids originating from these conveying channels. In the same way, the conveying channels 1440a', 1440c' have an angle of respectively 45° and minutes 45° relative to the separation channel 1450' in the plane of the separator.

The rectilinear separation channels 1450 and 1450' have a length of 22.5 mm allowing, during operation of the system, the cells, particles or molecules to become acoustically concentrated in the conveying channel 1470b then 1470d, the axes of which are identical to the axes of the separation channels.

Alternatively, the separator 1422 of the device 1400 comprises four recesses (not represented) made along the separation channels 1450 and 1450', and capable of each receiving an ultrasonic transducer (which are not represented). This embodiment makes it possible to obtain a standing wave in the separator 1422 if the latter is made of a material which does not reflect acoustic waves very much, the material being flexible and thin such as plastic, polymer or silicone materials. A silicone preferentially used is polydimethylsiloxane (PDMS). Preferentially, each ultrasonic transducer comprises a quarter-wave adapter plate of which the acoustic impedance is calculated so as to minimize the energy losses, and thus the heating, between the ultrasonic transducer and the walls of the device.

Preferentially, the cover plate (not represented) is made of PDMS or of molded plastic such as polycarbonate (PC), poly(methyl methacrylate) (PMMA), polypropylene (PP), polystyrene (PS), acrylonitrile butadiene styrene (ABS), cyclic olefin copolymer (COC), cyclic olefin polymer (COP) or polyoxymethylene (POM).

This device 1400 is capable of carrying out processes for preparing biological samples by acoustophoresis such as the process according to the invention. For this, all or part of the biological sample to be treated is introduced into the inlet orifice 1430a of the device 1400. A buffer solution is introduced into the inlet orifice 1430b, the buffer and the sample being introduced at respective flow rates capable of generating a laminar flow in the separation channel 1450. An ultrasonic transducer, such as a piezoelectric transducer, attached to the separation channel 1450 is then activated by a control signal, so as to carry out a step of separation of said biological sample by acoustophoresis. This separation makes it possible to promote the concentration of the non-specific particles, such as food debris, present in the sample, in the conveying channel 1470b of said acoustophoresis device. The decomplexified sample is obtained in the outlet orifice 1460a. A second step of separation of said concentrated sample by acoustophoresis is also carried out on the part resulting from the first separation in the channel 1450'. For this, a clean second buffer is simultaneously introduced into the inlet orifice 1430b' in order to extract the residual species of interest still present in the concentrated sample. This separation makes it possible to promote the concentration of the non-specific particles, such as food debris, still present in the concentrated sample, in the outlet orifice 1460c of said acoustophoresis device. The concentrated sample is then decomplexified a second time and then obtained in the outlet orifice 1460b. The collection and the mixing of the decomplexified samples from the outlet orifices 1460a and 1460b make it possible to increase the collection yield of the microorganisms initially present in the biological sample. Indeed, the microorganisms entrained with the non-specific particles during the first separation toward the channel 1450' via the channels 1440a' and 1440c' are capable of being separated by acoustophoresis in this channel 1450' and of thus being capable of being collected following this second separation in the orifice 1460b. The microorganism extraction yield is thus improved.

The relative position and the length of the second separation channel 1450' with respect to the main separation channel 1450' is chosen according to the desired applications, performances and flow rates. Advantageously, two buffer solutions of different type and density are introduced into the inlet orifices 1430b and 1430b'.

Figure 7A:
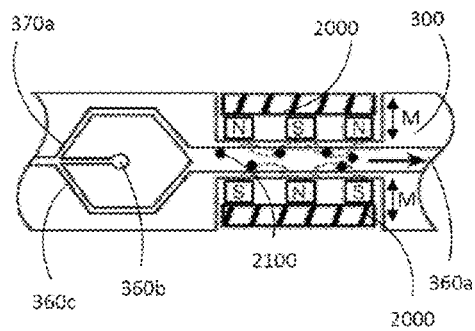
FIG. 7*a* represents a first alternative of production of the outlet orifices of the devices according to the invention.

Whatever the embodiment of the device according to the invention, the device may comprise, around the conveying channel toward an outlet orifice containing the decomplexified sample, mobile magnet supports which allow the capture of sample placed in the presence of magnetic particles such as magnetic silica. As represented in FIG. 7a, at the outlet of the device 300, two mobile magnet supports 2000 are placed in proximity to the orifice 360a. The magnets thus placed on each side of the conveying channel toward the outlet orifice 360a make it possible to capture microorganisms, in continuous flow, by movement of magnetic silica particles 2100 perpendicularly to the flow of the decomplexified sample. The movement M of the magnet supports is carried out for example perpendicularly to the channel and alternatively between the two supports in order to promote mixing of the sample and of the particles.

Figure 7B:
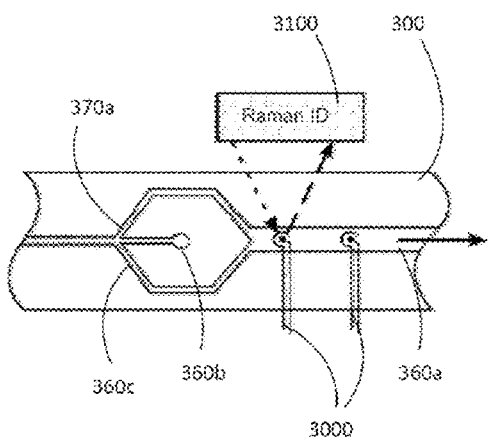
FIG. 7*b* represents a second alternative of production of the outlet orifices of the devices according to the invention.

Whatever the embodiment of the device according to the invention, the device may comprise, around the conveying channel toward an outlet orifice containing the decomplexified sample, dielectrophoresis (DEP) electrodes deposited on the surface of the device at the level of the outlet orifice. As represented in FIG. 7b, at the outlet of the device 300, two dielectrophoresis (DEP) electrodes 3000 are placed in proximity to the orifice 360a in order to make it possible to carry out a specific capture step. These electrodes can be either functionalized with capture antigens in the case of capture on a panel of desired species, or non-functionalized, then using only the well-known properties of capture by charge of the DEP technique. The identification of the species of interest which is (are) captured can, in the two situations, be confirmed or carried out for example by Raman identification 3100.

Figure 8:
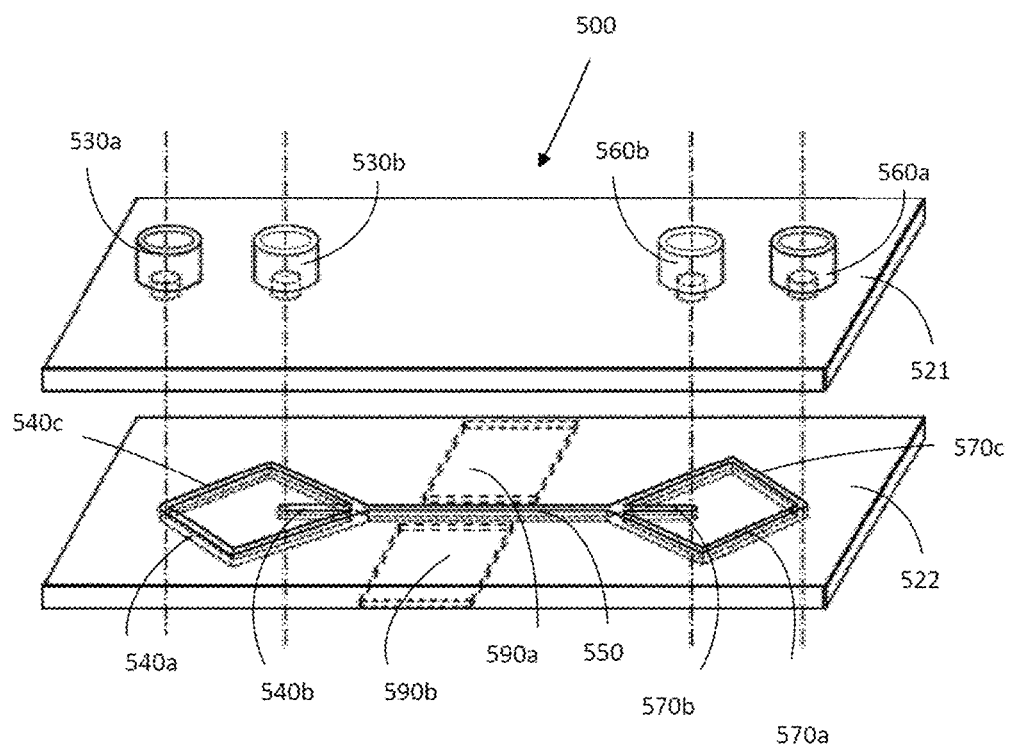
FIG. 8 represents a perspective view of a sixth microfluidic device with two inlet orifices according to the invention, capable of carrying out the process according to the invention.

As represented in FIG. 8, the invention also relates to a sixth device 500 comprising two fluidic parts, a separator 522 and a cover plate 521, these two parts being substantially planar. These two parts are assembled hermetically. Fluidic channels are made in the separator 522. The device 500 comprises two inlet orifices 530a, 530b, made in the cover plate 521, in fluidic communication with at least one separation channel 550 by means of conveying channels respectively 540a, 540c, for the orifice 530a and 540b for the orifice 530b. The separation channel 550 is also in fluidic communication with two outlet orifices 560a, 560b, by means of conveying channels, respectively 570a and 570c for the orifice 560a, 570b for the orifice 560b. The inlet and outlet orifices form reservoirs so as to be able to carry out operations of depositing a sample to be decomplexified by pipetting and the buffer solution and also operations of connecting to a system for pressurizing or placing under vacuum, servo-controlled and regulated on the basis of the flow rate measurement and making it possible to reproducibly control the introduction and the flow of the biological samples and of the buffer in the separation channel. The device 500 is arranged such that an ultrasonic transducer, not represented, can be integrated into or attached to a wall of said separation channel 550. The ultrasonic transducer thus integrated or attached is capable of transmitting mechanical oscillations in multiple acoustic waves that can act on the content of the separation channel and generate therein a standing acoustic wave. An alternating current generator, not represented, can be electrically connected to the transducer in order to generate a transducer control signal of which the frequency, the waveform and the amplitude are known.

In one particular embodiment of the device 500, the separator 522 is made of a glass plate 1 mm thick, coated with a layer of chromium and with a layer of photosensitive resin. After development of the photosensitive layer, the glass is etched with hydrofluoric acid (HF). The conveying channels 540a and 540c, 570a, 570c have a depth P of 125 µm, a lower width Lmin, at the bottom of the channels, of 300 µm, and an upper width Lmax of 550 µm in the plane of the separator in contact with the cover plate. The conveying channels 540b, 570b and also the separation channel 550 have a depth P of 125 µm, a lower width Lmin, at the bottom of the channels, of 375 µm, and an upper width Lmax of 625 µm in the plane of the separator in contact with the cover plate. The cover plate is pierced so as to produce the inlet and outlet orifices and then thermally bonded with the separator in order to produce a sealed assembly. The conveying channels of the inlet orifices (540a, 540b, 540c) have an angle of respectively 45°, 0° and minus 45° relative to the separation channel 550 in the plane of the separator, so as to slow down the flow rate of the fluids originating from the conveying channels having an angle of 45° or −45°, 540a, 540c, relative to the separation channel. The rectilinear separation channel 550 has a length of 80 mm, allowing the cells, particles or molecules to become acoustically concentrated in the conveying channel 570b during operation of the system. The axis of the conveying channel 570b is identical to the axis of the separation channel 550.

Alternatively, the separator 522 of the device 500 comprises two recesses, 590a, 590b, made along the separation channel 550, and capable of each receiving an ultrasonic transducer (which are not represented). This embodiment makes it possible to obtain a standing wave in the separator 522 if the latter is made of a material which does not reflect acoustic waves very much, the material being flexible and thin such as plastic, polymer or silicone materials. A silicone preferentially used is polydimethylsiloxane (PDMS). Preferentially, each ultrasonic transducer comprises a quarter-wave adapter plate of which the acoustic impedance is calculated so as to minimize the energy losses, and thus the heating, between the ultrasonic transducer and the walls of the device.

Preferentially, the cover plate (not represented) is made of PDMS or of molded plastic such as polycarbonate (PC), poly(methyl methacrylate) (PMMA), polypropylene (PP), polystyrene (PS), acrylonitrile butadiene styrene (ABS), cyclic olefin copolymer (COC), cyclic olefin polymer (COP) or polyoxymethylene (POM).

This device 500 is capable of carrying out processes for preparing biological samples by acoustophoresis such as the process according to the invention. For this, all or part of the biological sample to be treated is introduced into the inlet orifice 530a of the device 500. A buffer solution is introduced into the inlet orifice 530b, the buffer and the sample being introduced at respective flow rates capable of generating a laminar flow in the separation channel. An ultrasonic transducer, such as a piezoelectric transducer, attached to the separation channel is then activated by a control signal, so as to carry out a step of separation of said biological sample by acoustophoresis. This separation makes it possible to promote the concentration of the non-specific particles, such as food debris, present in the sample, in the outlet orifice 560b of said acoustophoresis device. The decomplexified sample is obtained in the outlet orifice 560a.

Figure 9:
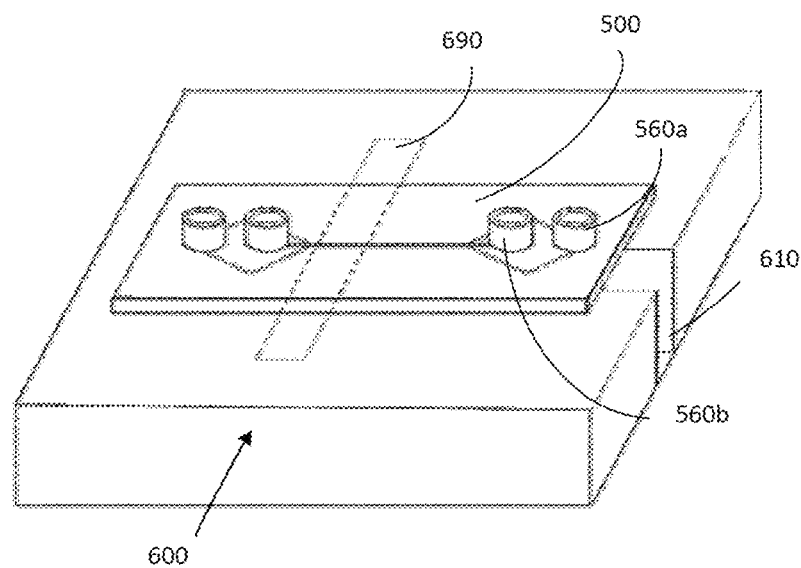
FIG. 9 represents a perspective view of a first support for microfluidic devices according to the invention, capable of carrying out the process according to the invention.

FIG. 9 represents a support 600 for devices with a device 500 placed and held on the support. This support makes it possible, for example, to treat one and the same biological sample simultaneously on several devices or several different samples simultaneously by connecting one or more reservoir(s) containing the sample(s), such as a syringe, to the various inlet orifices of the devices placed on the support. Alternatively, the support may comprise an articulated cap, not represented, which makes it possible to directly connect the inlet and outlet orifices of the device to pressurizing and/or vacuum means, on closing of the cap. This support comprises one or more bases (not represented) for receiving devices according to the invention, making it possible to place and hold said devices. The holding of the devices can be carried out mechanically or by suctioning the devices onto the receiving base(s). Ultrasonic transducers 690 can be placed in these bases so as to be able to create a standing wave in each of the devices placed on the support. The transducer is attached to the device when said device is placed in said base. Alternatively, a single ultrasonic transducer covering several devices can be placed in such a way as to be able to create a standing wave in each of the devices placed on the support.

A receiving space 610 makes it possible in particular to attach a heating system (not represented) to at least one of the outlet orifices of the device placed on the support. Said heating system makes it possible to incubate the biological sample treated and contained in at least one of the outlet orifices 560a, 560b. Furthermore, the receiving space 610 can comprise a means for measuring the optical density of the sample contained in at least one of the outlet orifices 560a, so as to avoid additional handling in order to carry out this operation. Furthermore, the support may be placed directly on a shaker or may comprise a shaking means so as to carry out a step of shaking the biological sample contained in one of the outlet orifices, before, during or following an incubation step.

This support 600 also makes it possible to place and maintain various devices 200, 300, 400, 500, 800, according to the invention, it being possible for the receiving space 610 to be easily adjusted by those skilled in the art.

Figure 10:
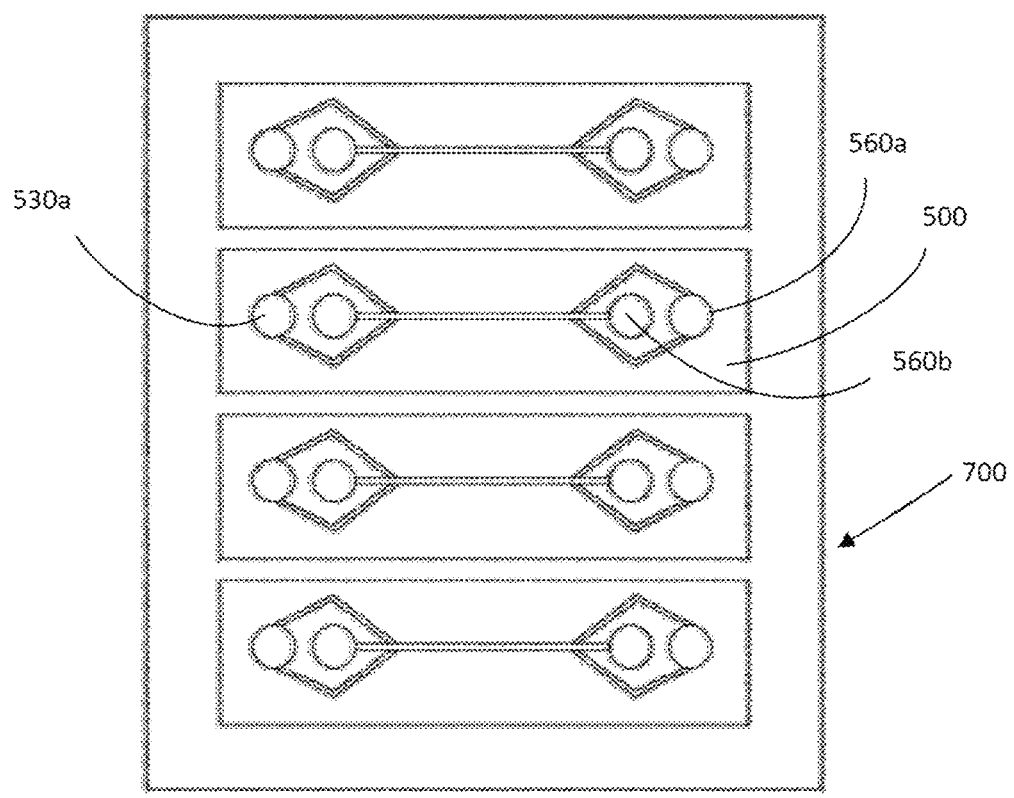
FIG. 10 represents a perspective view of a second support for microfluidic devices according to the invention, capable of carrying out the process according to the invention.

FIG. 10 presents a support 700 for devices according to the invention represented with four devices 500 placed and held on the support. This support makes it possible for example to treat one and the same sample simultaneously on several devices by connecting a reservoir containing the biological sample, such as a syringe, to the various inlet orifices 530a of the devices placed on the support. Alternatively, the support makes it possible to place the devices in such a way as to have each of the inlet and outlet orifices aligned on one and the same axis and according to a defined spacing. This spacing can advantageously be equivalent or multiple with respect to that of the pitch of a microplate known to those skilled in the art. In this way, the automatic or manual pipetting operations can be carried out directly in several devices simultaneously, in particular using a pipette or a microplate distributor. This support comprises several bases (not represented) for receiving devices according to the invention, making it possible to place and maintain said devices. Ultrasonic transducers (not represented), or one transducer common to several devices, can be placed in these bases so as to be able to create a standing wave in each of the devices placed on the support. The transducer is attached to the device when said device is placed in said base. In a manner identical to the support 600, the support 700 may comprise several receiving spaces (not represented) making it possible in particular to attach, to at least one of the outlet orifices of each of the devices placed on the support, a heating system (not represented) making it possible, for example, to incubate the biological sample treated and contained in at least one of the outlet orifices 560a, 560b. Furthermore, each of the receiving spaces may comprise a means for measuring the optical density of the sample contained in at least one of the outlet orifices 560a, so as to avoid additional handling in order to carry out this operation. Furthermore, the support 700 may be placed directly on a shaker or may comprise a shaking means so as to carry out a step of shaking the biological sample contained in one of the outlet orifices, before, during or following an incubation step. This support 700 also makes it possible to arrange in parallel several of the various devices 200, 300, 400, 500, 800, according to the invention, it being possible for the number of receiving bases to be easily adjusted by those skilled in the art. The various devices placed on the support 700 may be of the same type or of different types.

As represented in FIGS. 11, 12a and 12b, the invention also relates to a multiplex device 800 comprising three fluid parts, a separator 822, a cover plate 821 and a base 823, these three parts being substantially planar. These three parts are assembled hermetically. Fluidic channels are made in the separator 822. The device 800 comprises two inlet orifices 830a, 830b, in fluidic communication with eight separation channels 850, by means of a network of introduction channels 841, 842, and of conveying channels. Thus, the separation channels 850 communicate with the orifice 830a via the network of introduction channels 841 and also via the conveying channels 840a, 840c. In the same way, the separation channels 850 communicate with the orifice 830b via the network of introduction channels 842 and also via the conveying channel 840b. The separation channels 850 are also in fluidic communication with two outlet orifices 860a, 860b, by means of a network of suctioning channels 843, 844 and of conveying channels. Thus, the separation channels 850 communicate with the orifice 860a via the network of suctioning channels 843 and also via the conveying channels 870a, 870c. In the same way, the separation channels 850 communicate with the orifice 860b via the network of suctioning channels 844 and also via the conveying channel 870b. Eight separation channels 850 are represented, each of the channels 850 and of the associated suctioning channels forming a fluidic unit repeated eight times.

The device 800 is arranged so that an ultrasonic transducer, not represented, can be integrated into or attached to a wall of said separation channels 850. The ultrasonic transducer thus integrated or attached is capable of transmitting mechanical oscillations in multiple acoustic waves that can act on the content of each separation channel and generate therein a standing acoustic wave. An alternating current generator, not represented, can be electrically connected to the transducer in order to generate a transducer control signal of which the frequency, the waveform and the amplitude are known. Alternatively, through-openings 880 or etchings having a depth greater than or equal to that of the separation channels are made in the separator. These openings or etchings are distributed on each side of the separation channels 850. These openings 880 make it possible to obtain better acoustic separation of the resonances of each separation channel.

The networks of introduction channels 841, 842 make it possible to divide the flow, for example of biological sample or buffer introduced into the inlet orifices 830a and 830b. This parallelization of the separation channels makes it possible to treat a volume of sample by acoustophoresis at higher flow rates than on a conventional device, without degrading the extraction performance levels due to the increase in sample flow rate (in μl/min). Thus, if the networks divide the flow of sample introduced in half, conveying the sample to two separation channels, a flow rate that is twice as high can be achieved for one and the same level of decomplexification. In the same way, the suctioning networks 843, 844 make it possible to collect the samples or buffers treated in a single outlet orifice. These networks also make it possible to ensure a pressure equilibrium downstream of the step of separation by acoustophoresis.

This device 800 is capable of carrying out processes for preparing biological samples by acoustophoresis such as the process according to the invention. For this, all or part of the biological sample to be treated is introduced into the inlet orifice 830a of the device 800. A buffer solution is introduced into the inlet orifice 830b, the buffer and the sample being introduced at respective flow rates capable of generating a laminar flow in the separation channels. An ultrasonic transducer, such as a piezoelectric transducer, attached to the separation channels is then activated by a control signal, so as to carry out a step of separation of said biological sample by acoustophoresis. This separation makes it possible to promote the concentration of the non-specific particles, such as food debris, present in the sample, in the outlet orifice 860b. The decomplexified sample is obtained in the outlet orifice 860a. Since this device has eight separation channels, a biological sample treatment flow rate eight times higher than a prior art device can be achieved on one and the same device. In the same way, a volume of sample (in ml) eight times higher can be treated in an identical time without flow rate modification (μl/min), thus keeping the extraction performance levels intact.

More generally, this fifth multiplex device comprises two inlet orifices in fluidic communication with at least two separation channels, by means of a network of introduction channels and conveying channels. Said separation channels also communicate with two outlet orifices by means of a network of suctioning channels and of conveying channels. This implementation unit associated with each of the separation channels makes it possible to adjust the sample treatment flow rate according to the desired application, by multiplying the number of parallelized separation channels and of associated conveying channels.

As represented in FIGS. 13a and 13b, the invention also relates to a connecting device 900 which makes it possible to connect orifices of a microfluidic device to an introduction or suctioning means. This device is represented connected to a device 10 of the prior art.

The connecting device 900 comprises an inlet connector 910 and an outlet connector 920. The inlet connector 910 comprises three conveying channels 930a, 930b, 930c capable of cooperating with the inlet orifices of the device 10, respectively 30a, 30b, 30c. The inlet connector 910 thus makes it possible to connect means for introducing biological sample or buffer solution without directly handling the microfluidic device 10. For example, an introduction tube of a syringe 931b, visible in FIG. 13b, is connected to the conveying channel 930b in order to be able to introduce a solution into the orifice 30b. A similar arrangement is carried out facing the inlet orifices 30a and 30c in order to be able to introduce the biological sample into the inlet orifices 30a and 30c.

The outlet connector 920 comprises three conveying channels 960a, 960b, 960c capable of cooperating with the outlet orifices of the device 10, respectively 60a, 60b, 60c. The outlet connector 920 thus makes it possible to connect means for suctioning or means for collecting biological sample or buffer solution without directly handling the microfluidic device 10 and without requiring a suctioning or pumping means connected at the outlet of the microfluidic device. For example, a collecting tube 961b visible in FIG. 13b, such as an "Eppendorf" tube, is placed facing the conveying channel 960b in order to be able to collect the solution originating from the outlet orifice 60b. A similar arrangement is carried out facing the outlet orifices 60a and 60c in order to collect the decomplexified sample directly in collecting tubes.

The device 10 is placed between the connectors 910 and 920 and a support, not represented. The connectors 910 and 920 are held on said support by any means, in particular by screwing, by force fitting or by return springs, so as to provide a hermetic connection with the entry and outlet orifices of the device. Advantageously, the connectors comprise O-ring seals 990 in order to guarantee this leaktightness when the connector is held.

Of course, the geometry of this connecting device 900 and of the connectors 910 and 920 and the number of conveying channels of the connectors may easily be adjusted so as to be used with one or more devices 200, 300, 400, 500, 800 according to the invention.

Figure 14:
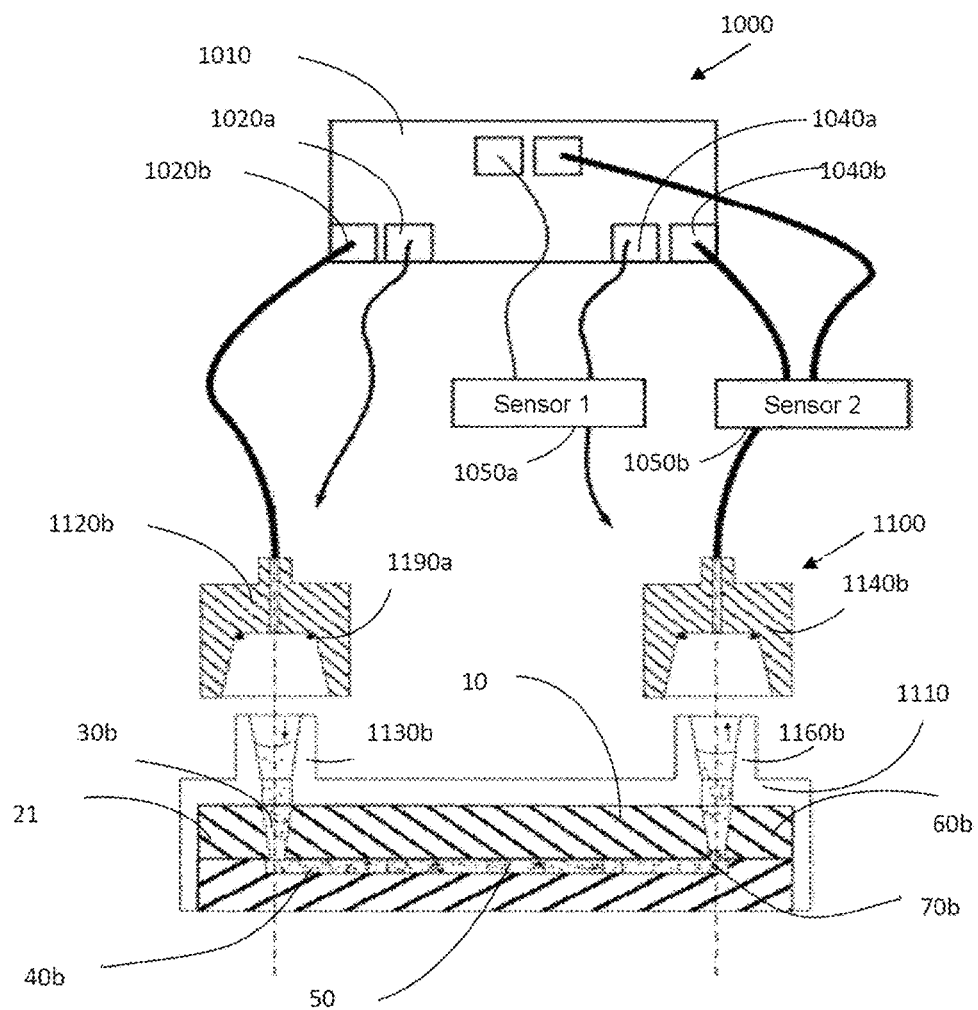

As represented in FIG. 14, the invention also relates to an air regulation system 1000 and associated connecting devices 1100 making it possible to carry out the method according to the invention by servo-control of the introduction and of the suctioning of the liquids introduced. The system is in this case represented with a device 10 of the prior art represented here along section A-A of FIG. 1.

The regulation system 1000 comprises a pressure or vacuum generator 1010. The generator 1010 comprises two pressure outlets 1020a and 1020b capable of delivering the air pressure required for the introduction of the biological sample or of the buffer solution of a method according to the invention at a regulated flow rate in a microfluidic device. The generator 1010 also comprises two vacuum inlets 1040a and 1040b capable of generating an air pressure differential sufficient to suction the biological sample and the buffer solution of a method according to the invention at a regulated flow rate in a microfluidic device. For these purposes, the vacuum inlets 1040a and 1040b are connected to the device via two air flow sensors 1050a and 1050b in order to measure and to servo-control the regulation of air pressure introduced or the vacuum for suctioning of the sample and of the buffer solution of a method according to the invention. This regulation thus makes it possible to obtain a constant flow rate of separation and of decomplexification of the biological sample while limiting the pressure drop risks.

For this purpose, the generator is connected to the two inlet and outlet orifices of the device by means of the connecting device 1100. This device comprises a connector for inlet via inlet orifice and also a connector for outlet via outlet orifice. Only the inlet connectors 1120b and 1140b are represented in the interests of clarity of the figure.

The connecting device 1100 also comprises a cap 1110 placed and held on the device 10. The cap 1110 comprises a reservoir opposite each of the inlet and outlet orifices of the device 10. Only the reservoir 1130b cooperating with the orifice 30b and the reservoir 1160b cooperating with the orifice 60b are represented in the interests of clarity of the figure. The cap 10 can be made of plastic, for example by injection-molding, and makes it possible to cap a device in order to present reservoirs opposite each inlet and outlet orifice of the device held. These reservoirs can in particular be used for depositing and collecting samples and buffer solutions. The cap is held on a support, not represented, in such a way as to make a hermetic connection with the orifices of the device 10. The cap can be held on the support by any means, in particular by screwing, by force fitting or by the pressure of a return spring.

An inlet connector 1120b is capable of being placed and held on the cap 1110 so as to cooperate with the reservoir 1130b of said cap. An outlet connector 1140b is also capable of being placed and held on the cap 1110 so as to cooperate with the reservoir 1160b of said cap. The connectors advantageously have O-ring seals for leaktightness and are held on the cap by screws or springs. The connectors can also be held on the cap by any means, in particular by screwing, by force fitting or by the pressure of a return spring.

Of course, the geometry of this connecting device 1100 and in particular of the connectors may be easily adjusted so as to be used with a device 200, 300, 400, 500, 800 according to the invention.

The examples hereinafter will make it possible to understand the present invention more clearly. However, these examples are given only by way of illustration and should in no way be regarded as limiting the scope of said invention in any way.

Example: Treatment of Food Samples

A) Assembly of a Device for Carrying Out the Process According to the Invention

A microfluidic device is produced in accordance with the device represented in FIG. 1.

Figure 3:
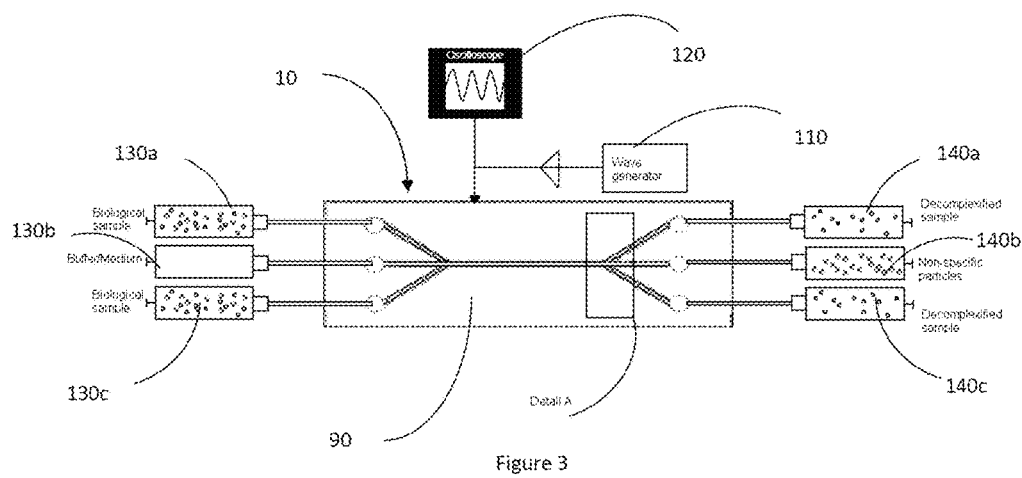
FIG. 3 represents a diagrammatic view of a system for carrying out a method according to the present invention using a microfluidic device according to the prior art.

As illustrated in FIG. 3, the three inlet orifices 30a, 30b, 30c, and the three outlet orifices 60a, 60b, 60c, are connected to introduction means, such as syringes (Becton Dickinson Plastipak™, Spain) via an assembly comprising a pipette tip (Eppendorf, United Kingdom) connected to a Tygon tube (ID 0.03, OD 0.09 Cole-Parmer, United Kingdom). A pipette tip is hermetically bonded to each of the orifices, a Tygon tube is then inserted into and then bonded in the pipette tip and, finally, assembled with the syringe end piece. In this way, three introduction syringes 130a, 130b, 130c make it possible to introduce a fluid into each of the inlet orifices 30a, 30b, 30c, while three suctioning means such as syringes 140a, 140b, 140c make it possible to suction the fluid in each of the outlet orifices 60a, 60b, 60c. Alternatively, a connecting device 900 can be used to connect each syringe to the device.

The three suctioning syringes 140a, 140b, 140c make it possible to ensure a pressure equilibrium, and a flow rate equilibrium, in the three conveying channels to the outlet orifices, downstream of the separation channel. In this way, the device is less subject to possible blockages that can be due to large particles hindering the circulation of the fluid in one of the channels.

Syringe pumps (Harvard Apparatus, United Kingdom), not represented, are used to control the sample and buffer introduction flow rates.

A piezoelectric transducer with dimensions of 10 mm×30 mm, made of ceramic (Pz26, Ferroperm Piezoceramics, USA), with a resonance frequency range of 1 MHz to 2 MHz is attached to the device 10 by an ultrasound gel (Anagel™ United Kingdom). This transducer makes it possible to generate ultrasound used to induce a standing wave between the walls of the separation channel. Motion of the particles induced by the acoustophoresis phenomenon can thus be obtained by applying an alternating current (AC) to the transducer. This control signal is introduced into the circuit by a function generator (Agilent, model 33210A, 10 MHz on the function/generator of arbitrary waveform, United Kingdom) in sinusoidal operating mode. An amplifier (Amplifier research, model 1W1000B, 1-1000 MHz, AR) is used to amplify the signal originating from the function generator and to obtain the required amplitude for entraining the particles. An oscilloscope (Tektronix, model 1042 SCT, USA) is connected in parallel with the sensor in order to measure the operating voltage.

B) Preparation of Chicken and Beef Food Samples

Various chicken parts (wings, thighs with the skin, white meat with and without the skin and also neck skin) were purchased from three suppliers in order to form a first batch of samples, referenced according to the chicken part tested. For each sample of this batch, a 10 g fraction is weighed and placed in a TEMPO® bag (bioMérieux, France, Ref. 80015), then mixed with 90 ml of buffered peptone water (BPW; bioMérieux, France, Ref. 42042). The whole mixture is then homogenized in a "grinder-homogenized" system (Masticator; IUL Instruments, Germany) set at 0.7 for 30 s.

After homogenization, a step of enrichment of the sample is carried out by incubation for 4 h at 37° C. and then an aliquot fraction of 10 ml of enriched broth taken from the side of the filtered part of the TEMPO® bag is recovered (the TEMPO® bag having a lateral filter allowing prefiltration of the sample). No subsequent filtration step is carried out on this batch.

A second batch of samples, prepared as above and obtained by mixing 10 g of ground beef and 90 ml of BPW, is prepared in the same way as the first sample batch.

C) Preparation of Inoculated Samples

In order to prepare an inoculated sample containing a controlled inoculum of pathogenic organisms, an isolated colony of *Salmonella typhimurium* (NCTC 12023/ATCC® 14028, Pro-lab Diagnostics, UK) isolated from a culture on Trypticase Soy Agar culture medium (TSA; bioMérieux, ref. 43011, France) is suspended in 9 ml of Trypticase Soy Broth (TSB; bioMérieux, ref. 42100, France) then incubated at 37° C. for 18 h. Approximately 0.2 ml of enriched broth thus obtained is diluted in 9 ml of BPW and its absorbance at 600 nm is measured (CECIL 1011 apparatus, series 1000) so as to obtain a value of 0.070 corresponding to approximately $1.5 \times 10^8$ CFU·ml$^{-1}$. From this enriched broth, 5 series of dilutions are then prepared and numbered from d-1 to d-5 corresponding to concentrations of $10^7$ to $10^3$ CFU·ml$^{-1}$ (CFU meaning colony forming units).

In order to determine the amount of pathogens present in the batch of sample containing a controlled inoculum thus obtained, a TSA culture medium is inoculated with 100 μl of d-5 and incubated at 37° C. overnight. This step is carried out in duplicate. The actual number of microorganisms present in the initial sample was calculated according to the dilution and the number of colonies counted on the medium.

Using these dilutions containing pathogenic agents, a first series of 10 ml of chicken broth enriched by incubation (prepared as described above) was inoculated with 0.1 ml of $10^6$ CFU·ml$^{-1}$ of *Salmonella typhimurium* so as to obtain a final concentration of $10^4$ CFU·ml$^{-1}$.

A second series of 10 ml of chicken broth mixed with BPW and prepared without the incubation step has 0.1 ml of $10^5$ CFU·ml$^{-1}$ of *Salmonella typhimurium* added to it so as to obtain a final concentration of $10^3$ CFU·ml$^{-1}$.

In the same way, 10 ml of beef broth at $10^3$ CFU ml$^{-1}$ are prepared, without the incubation step, as are samples at $10^4$ CFU ml$^{-1}$, with the incubation step.

For carrying out the treatment method according to the invention, 0.5 ml of chicken sample are introduced, via two syringes, into the inlet orifices 30a and 30c of a device as described above at a flow rate of 10 μl·min$^{-1}$ via the conveying channels 40a, 40c. A BPW broth is introduced, via a syringe, into the inlet orifice 30b at a flow rate of 30 µl·min$^{-1}$.

For carrying out the treatment method according to the invention, 0.5 ml of beef sample are introduced, via two syringes, into the inlet orifices 30a and 30c of a device as described above at a flow rate of 10 µl·min$^{-1}$ via the conveying channels 40a, 40c. A BPW broth is introduced, via a syringe, into the inlet orifice 30b at a flow rate 30 µl·min$^{-1}$.

When no control signal is applied to the ultrasonic transducer, the non-specific chicken or beef debris are predominantly in the outlet orifices 60a and 60c.

Figure 15:
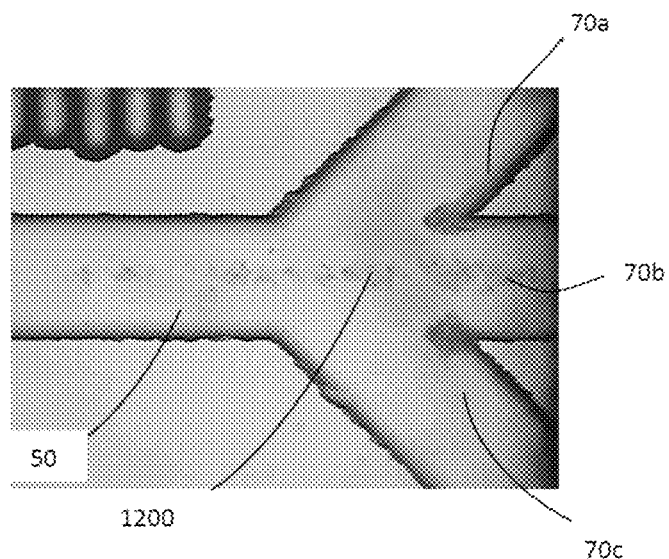
FIG. 15 is a photograph viewed from above of a part of the microfluidic device of the system according to detail A of FIG. 3, during the method according to the invention.

When a control signal is applied to the ultrasonic transducer, of 1.303 MHz and of amplitude 37.4 V peak-to-peak (Vp-p) in order to subject the debris to an acoustophoresis step, and as shown in FIG. 15, a laminar flow of chicken debris 1200 is observed in the separation channel 50 and in the conveying channel 70b in the direction of the outlet orifice 60b. A similar phenomenon can be observed with the debris present in the beef samples. This observation is confirmed by measuring the optical density at 600 nm at the various outlet orifices.

On the basis of the optical densities (ODs) measured, a calculation of the sample decomplexification rate can be carried out according to the following relationship:

$$\text{Decomplexification rate (\%)} = 100 \times \frac{(\text{Mean } OD)[\text{without ultrasound}] - (\text{Mean } OD)[\text{with ultrasound}]}{(\text{Mean } OD)[\text{without ultrasound}]}$$

D) Decomplexification of Chicken and Beef Food Samples

Figure 16A:
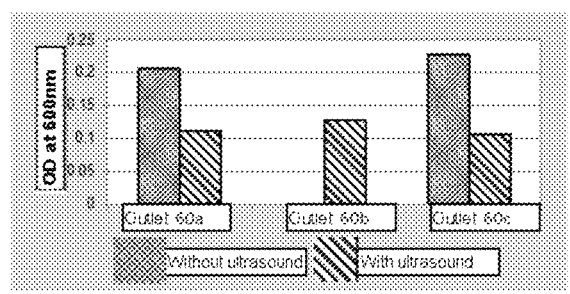
FIG. 16a presents the optical density values in the various outlet orifices for a chicken sample treated according to the method of the invention.
Figure 16B:
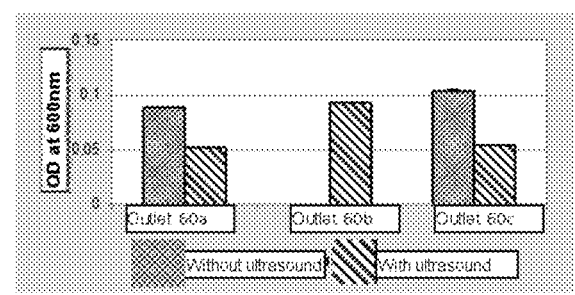
FIG. 16b presents the optical density values in the various outlet orifices for a sample of beef treated according to the method of the invention.
Figure 17:
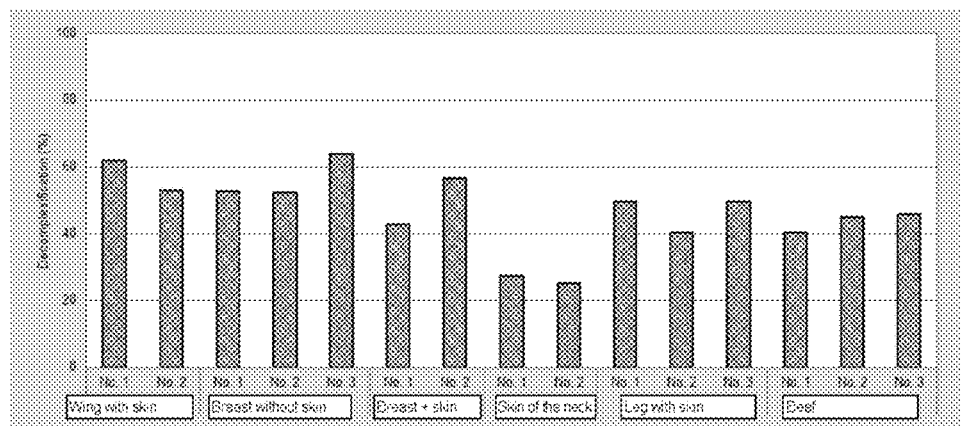
FIG. 17 presents the decomplexification values according to the chicken or beef parts treated according to the method of the invention.

The results thus calculated are presented in FIG. 16a for the treatment of the chicken samples at 10$^3$ CFU ml$^{-1}$ and FIG. 16b for the treatment of beef samples at 10$^3$ CFU ml$^{-1}$. These operations are reproduced two to three times depending on the sample. These results confirm the capacity of the method according to the invention to separate and concentrate the debris in at least one of the outlet orifices, in this case the outlet orifices 60a and 60c. A decomplexification rate of between 20% and 62% is in fact noted in FIG. 17.

E) Viability of the Microorganisms Present in Chicken and Beef Food Samples

Figure 18:
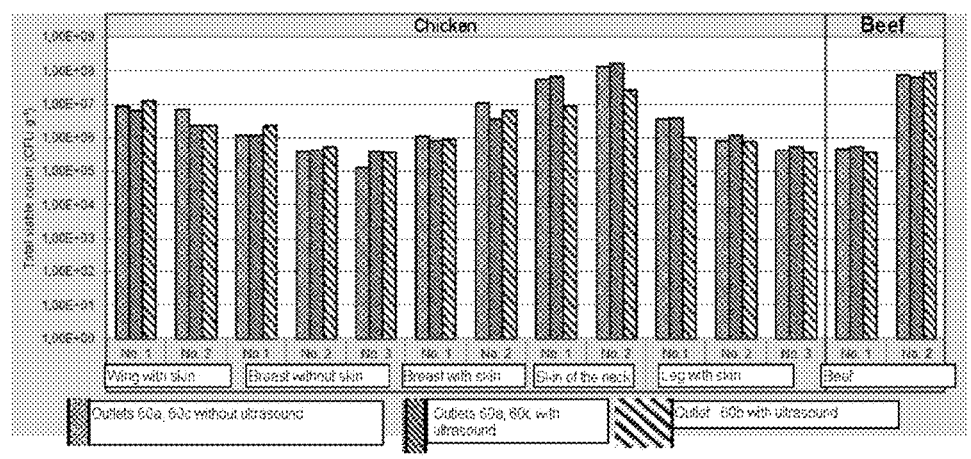
FIG. 18 presents the values in colony forming units per gram ($CFU \cdot g^{-1}$) of the total viable count of the flora according to the method of the invention.

After having demonstrated the capacity for sample decomplexification by the method according to the invention, various sample series made it possible to confirm the viability of the intrinsic flora present in the samples treated by acoustophoresis according to the method described above. Comparative tests between a sample treated with the method according to the invention and one and the same sample having circulated in the device without being separated by acoustophoresis were thus carried out. Following these tests, the samples collected in the outlet orifices of the device were collected and inoculated onto TSA agars (bioMérieux, Ref. 43011, France) for the total viable count of the flora contained in the samples after enrichment. Whatever the sample, chicken or beef, viable colonies were observed only in the outlet orifices 60a and 60c when the separation by acoustophoresis was not activated. This confirms that the flow rates of circulation of the fluids in the separation channel allow a laminar flow along the entire length of the separation channel to become set up, avoiding any mixing between the fluids. When the separation by acoustophoresis is activated, viable microorganisms were found in the samples originating from the three outlets 60a, 60b, 60c, suggesting that a part of the microorganisms and also the debris present in the sample undergo an acoustic focusing effect. These results are illustrated in FIG. 18 and reproduced two or three times according to the types of samples. The method according to the invention thus allows rapid preparation of food samples, even very complex food samples such as chicken neck skin, without impact on the intrinsic flora and allowing subsequent detection steps.

Figure 19A:
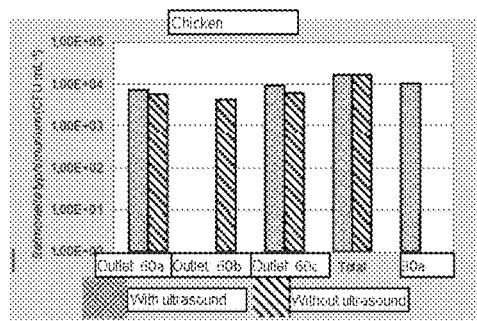
FIG. 19a presents the values in colony forming units per milliliter ($CFU \cdot ml^{-1}$) of counting *Salmonella typhimurium* according to the method of the invention for chicken samples.
Figure 19B:
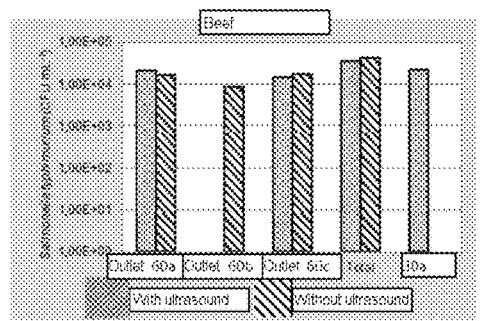
FIG. 19b presents the values in colony forming units per milliliter ($CFU \cdot ml^{-1}$) of counting *Salmonella typhimurium* according to the method of the invention for beef samples.

F) Treatment of Chicken and Beef Food Samples Containing Pathogenic Microorganisms The objective of the food sample treatment is to be capable of separating the intrinsic flora from the particles of interest, in particular from the pathogenic agents. Various series of samples made it possible to confirm the viability of the pathogenic agents present in the samples treated by acoustophoresis according to the method described above. For this, colonies of *Salmonella typhimurium* were subsequently added to a chicken sample enriched with the BPW medium, as described above, and incubated at 37° C. for 4 h in order to obtain a final concentration of 10$^6$ CFU·ml$^{-1}$. In the same way as for the non-inoculated samples, 18% and 36% decomplexification rates were observed on these samples containing *Salmonella typhimurium* colonies. The total number of viable colonies, obtained by inoculating and counting on TSA media (bioMérieux, France), also shows the non-invasive aspect of the preparation method as described in the invention. In addition to the observation of the total number of viable colonies, a part of the decomplexified samples (originating from the side outlets) and of the concentrated samples (originating from the central outlet) were plated out onto a chromID®-*Salmonella* chromogenic medium (bioMérieux, Ref. 43621, France) in order to identify the viability of the pathogenic agents downstream of the sample preparation according to the invention. A high level of *Salmonella typhimurium* recovered in the outlet orifices was noted with a slightly lower level of the pathogenic agent escaping via the outlet orifice 60b where the debris is also more concentrated than the outlet orifices 60a and 60c, (FIG. 19a and FIG. 19b).

The demonstration of a high level of recovery of *Salmonella typhimurium* and also the separation thereof from the intrinsic flora by means of a step of culturing on a plate are thus demonstrated.

G)—Viability of Microorganisms at Low Concentration in Chicken and Beef Food Samples A series of experiments is also carried out on inoculated samples having a lower concentration level of target pathogenic microorganisms. For this, samples having a pathogen concentration of 10$^2$-10$^3$ CFU·mL$^{-1}$ are prepared in the enriched food matrix sample.

Figure 20:
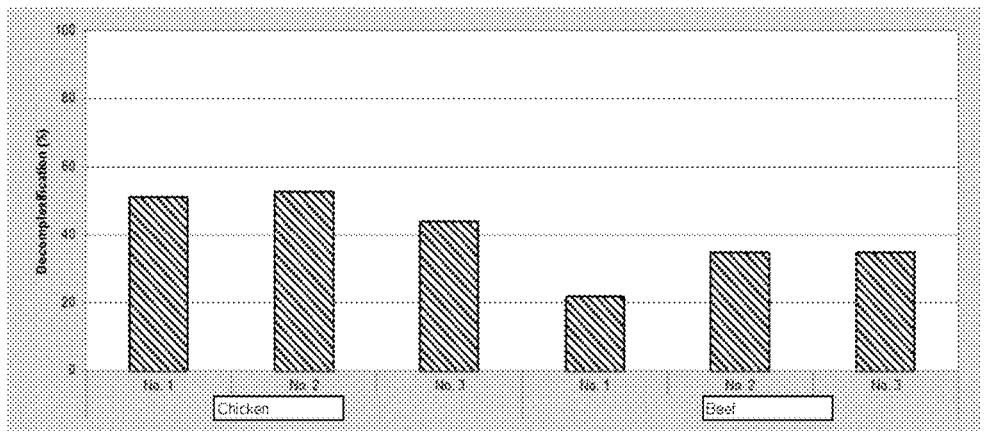
FIG. 20 presents the decomplexification values for chicken or beef samples treated according to the method of the invention.
Figure 21:
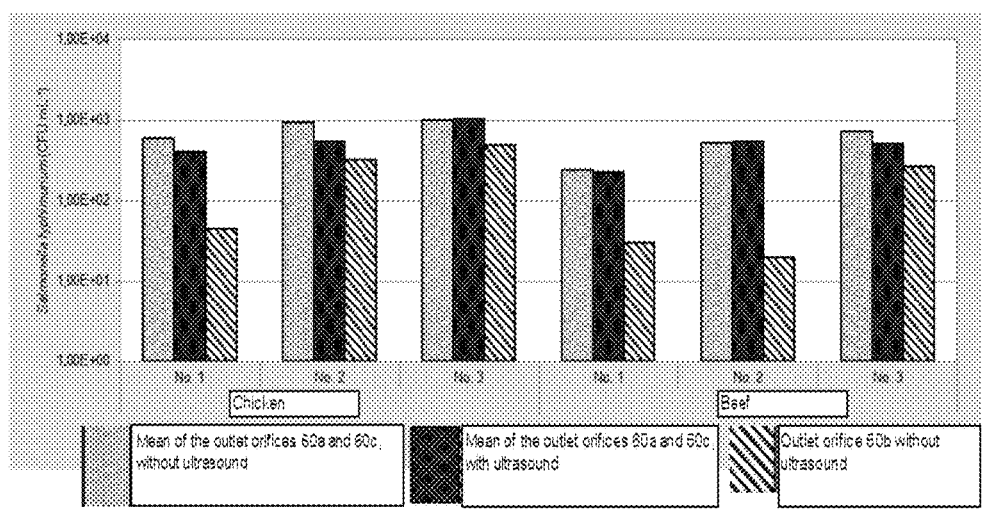
FIG. 21 presents the values in colony forming units per milliliter ($CFU \cdot ml^{-1}$) of counting *Salmonella typhimurium* according to the method of the invention for chicken and beef samples.

These samples were prepared by mixing 10 g of skinless chicken samples or of beef samples with 90 ml of BPW medium, and were homogenized using a grinder-homogenizer (Masticator, IUL, Germany) and treated without incubation step. 0.1 ml of approximately 10$^5$ CFU·mL$^{-1}$ of *Salmonella typhimurium* was then inoculated into 10 ml of sample enriched with BPW in order to obtain the final concentration of 10$^3$ CFU·ml$^{-1}$. A decomplexification rate of 20% to 50% by means of the method according to the invention was also observed (FIG. 20). In the same way as in the previous experiment on samples at a high concentration, a very high level of *Salmonella typhimurium* could be recovered in the outlet orifices 60a and 60c, according to a factor of 5 to 10 relative to the outlet orifice 60b (FIG. 21).

These samples thus show the advantage of the method for treating biological samples according to the invention. Said method thus makes it possible, using a microfluidic device having a separation channel that is sufficiently wide to prevent the non-specific particles from creating a blockage and combined with an acoustic wave having a frequency of approximately 1.3 MHz, to decomplexify a food sample while at the same time guaranteeing the viability of the intrinsic flora and of the pathogenic agents that may be present, even at low concentration of pathogenic agent. This decomplexification is in addition carried out at a rapid flow rate, of approximately 2 ml·h$^{-1}$ and can be carried out continuously, without cleaning and without risk of blockage. The resolution of microorganisms from the food matrices is also sufficient to make the method according to the invention a standard protocol, not requiring adjustment according to the types of food samples treated.

Method for Treating Biological Samples, Especially Food Samples

The present invention concerns a method for treating a biological sample, preferably a food sample which may contain one or more species of interest, comprising a step of decomplexification by acoustophoresis.

FIG. 3

The invention claimed is:

1. A method for treating a food sample which may contain one or more microorganisms of interest and non-specific particles, the treatment method comprising a step of decomplexification, wherein the decomplexification comprises:
   a) introducing all or part of the food sample into a first inlet orifice of an acoustophoresis device,
   b) introducing a buffer solution into a second inlet orifice of the acoustophoresis device, the inlet orifices being fluidically connected to at least two outlet orifices by a separation channel,
   c) introducing the buffer and the food sample at respective flow rates capable of generating a laminar flow in the separation channel, and
   d) carrying out a step of separation of the microorganisms and the nonspecific particles in the food sample by acoustophoresis so as to promote the concentration of the non-specific particles present in the food sample in at least one of the outlet orifices of the acoustophoresis device, wherein the method further comprises:
   e) a step of carrying out an enrichment of the microorganisms of interest in the food sample before the introduction of the food sample into the acoustophoresis device, and
   f) a step of lysing the microorganisms of interest following the separation step.

2. The treatment method as claimed in claim 1, further comprising a step of counting the total microorganisms present in the food sample following the separation step and before the lysis step.

3. The treatment method as claimed in claim 1, further comprising a step of specific or non-specific capture of the one or more microorganisms of interest on a capture support followed by a step of concentration by immunological separation.

4. The treatment method as claimed in claim 1, further comprising a step of amplification and analysis of the lysed sample.

5. The treatment method as claimed in claim 1, further comprising a step of analysis of the one or more captured microorganisms of interest.

6. The treatment method as claimed in claim 1, further comprising a step of labeling with a fluorescent label the one or more microorganisms of interest, the fluorescent label being specific to the microorganisms of interest, following the step of separation by acoustophoresis.

7. The treatment method as claimed in claim 6, further comprising a step of analysis by flow cytometry aimed at detecting the presence of the fluorescent label.

8. The treatment method as claimed in claim 1, the food sample being prefiltered through a filter or a membrane before the introduction of the food sample into the acoustophoresis device.

9. The treatment method as claimed in claim 1, the food sample being homogenized before the introduction of the biological sample into the acoustophoresis device, the introduction being carried out without prior filtration step.

10. The treatment method as claimed in claim 1, further comprising carrying out a second step of separation by acoustophoresis of the food sample by reintroduction of the sample into the separation channel of the device or by introduction of the sample into a second channel of separation by acoustophoresis.

11. The treatment method as claimed in claim 10, the second step of separation by acoustophoresis being carried out with a buffer different than the first step.

12. The treatment method as claimed in claim 3, wherein the specific capture of the one or more microorganisms of interest is implemented on a magnetic capture support.

13. The treatment method as claimed in claim 4, wherein the amplification and analysis of the lysed sample are implemented by quantitative PCR.

14. The treatment method as claimed in claim 5, wherein the analysis of the one or more captured microorganisms of interest is by means of one or more immunoassays specific for the one or more captured microorganisms of interest.

* * * * *